United States Patent
Mikawa

(10) Patent No.: US 8,420,319 B2
(45) Date of Patent: *Apr. 16, 2013

(54) ASYMMETRIC ADAPTER LIBRARY CONSTRUCTION

(75) Inventor: Gi Mikawa, Cambridge (GB)

(73) Assignee: Population Genetics Technologies Ltd, Cambridge (GB)

( * ) Notice: Subject to any disclaimer, the term of this patent is extended or adjusted under 35 U.S.C. 154(b) by 0 days.

This patent is subject to a terminal disclaimer.

(21) Appl. No.: 13/610,410

(22) Filed: Sep. 11, 2012

(65) Prior Publication Data

US 2013/0029380 A1 Jan. 31, 2013

Related U.S. Application Data

(63) Continuation of application No. 13/224,134, filed on Sep. 1, 2011, now Pat. No. 8,288,097, which is a continuation of application No. 12/432,080, filed on Apr. 29, 2009, now Pat. No. 8,029, 993.

(60) Provisional application No. 61/049,323, filed on Apr. 30, 2008.

(51) Int. Cl.
*C12Q 1/68* (2006.01)
*C12P 19/34* (2006.01)
*C07H 21/00* (2006.01)

(52) U.S. Cl.
USPC .......... 435/6.1; 435/91.1; 435/91.2; 536/23.1

(58) Field of Classification Search ............ 435/6.1, 435/91.1, 91.2; 536/23.1
See application file for complete search history.

(56) References Cited

U.S. PATENT DOCUMENTS

| 5,712,126 | A | 1/1998 | Weissman et al. |
| 6,372,434 | B1 | 4/2002 | Weissman et al. |
| 6,773,886 | B2 | 8/2004 | Kaufman et al. |
| 6,777,180 | B1 | 8/2004 | Fisher et al. |
| 7,217,522 | B2 | 5/2007 | Brenner |
| 7,803,550 | B2 | 9/2010 | Makarov et al. |
| 7,993,842 | B2 | 8/2011 | McKernan et al. |
| 8,288,097 | B2 * | 10/2012 | Mikawa ................. 435/6.1 |
| 2003/0046724 | A1 | 3/2003 | Ranch et al. |
| 2004/0209299 | A1 | 10/2004 | Pinter et al. |
| 2006/0024681 | A1 | 2/2006 | Smith et al. |

(Continued)

FOREIGN PATENT DOCUMENTS

| WO | 2004081183 | 9/2004 |
| WO | 2005068656 | 7/2005 |
| WO | 2007087262 | 8/2007 |
| WO | 2009032167 | 3/2009 |

OTHER PUBLICATIONS

Head, et al., "Method for improved Illumina sequencing library preparation using NuGEN Ovation RNA-Seq System", Biotechniques, 2011, 50:177-80.
Kundu, et al., "Cleavable substrate containing molecular beacons for the quantification of DNA-photolyase activity", Chembiochecm, 2002, 3:1053-60.

(Continued)

*Primary Examiner* — Jezia Riley
(74) *Attorney, Agent, or Firm* — James S. Keddie; Bozicevic, Field & Francis LLP

(57) ABSTRACT

The present invention provides methods and compositions for asymmetrically tagging a nucleic acid fragment using asymmetric adapters.

13 Claims, 12 Drawing Sheets

U.S. PATENT DOCUMENTS

| | | |
|---|---|---|
| 2006/0101540 A1 | 5/2006 | Ranch et al. |
| 2007/0128624 A1 | 6/2007 | Gormley et al. |
| 2007/0172839 A1 | 7/2007 | Smith et al. |
| 2007/0231823 A1 | 10/2007 | McKernan et al. |
| 2008/0051294 A1 | 2/2008 | Gormley et al. |
| 2011/0105364 A1 | 5/2011 | Kurn |
| 2012/0122161 A1 | 5/2012 | Musgrave-Brown et al. |
| 2012/0196279 A1 | 8/2012 | Underwood et al. |

OTHER PUBLICATIONS

Margulies, M. et al., "Genome sequencing in microfabricated high-density picolitre reactors" Nature, vol. 437; Sep. 15, 2005; pp. 376-380.

Sipa et al., "Effect of base modifications on structure, thermodynamic stability, and gene silencing activity of short interering RNA" (2007) RNA (Cold Spring Harbor) vol. 13, No. 8, pp. 1301-1316.

* cited by examiner

Top strand: SEQ ID NO:1
Bottom Strand: SEQ ID NO:2

5' – TAATACGACTCACTATAGGGAGA - 3'
Reverse Primer (410: SEQ ID NO:3)

5' – CCAATTAACCCTCACTAAAGGGAGAAGCCAATCGA - 3'
T3 Promoter Primer (complement to 412: SEQ ID NO:4) (see element 502 in Figure 15)

dG = -8.467  dH = -310.6 A-B

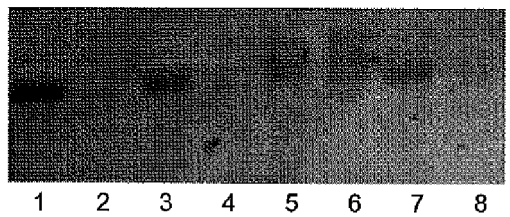

Lane 1. R strand
Lane 2. R strand treated with ExoI
Lane 3. R strand treated with Lambda Exo
Lane 4. R strand treated with ExoI + Lambda Exo
Lane 5. Asymmetric adapter annealed between bottom T and top strand R.
Lane 6. Asymmetric adapter treated with ExoI
Lane 7. Asymmetric adapter treated with Lambda Exo
Lane 8. Asymmetric adapter treated with ExoI + Lambda Exo

FIG. 10

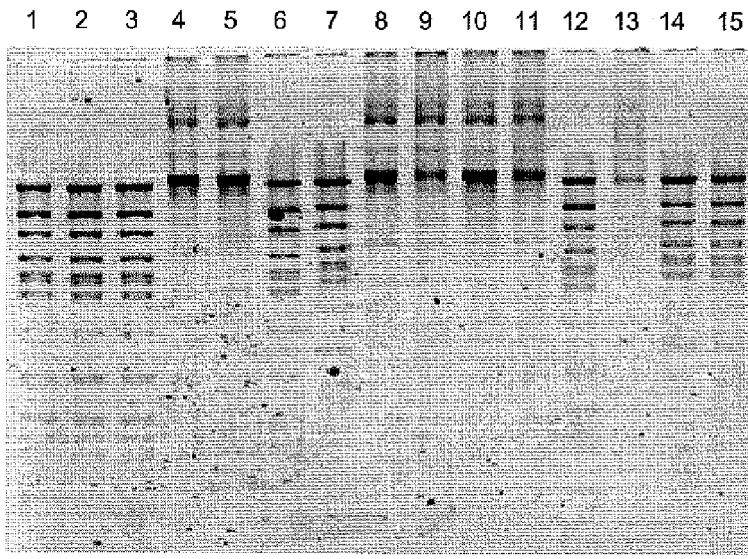

01. lambda DNA *Bst*YI digestion
02. Fill-in control: no sequenase
03. Fill-in with dGTP with sequenase
04. Ligation control: ligase +, adapter −, using fill-in control of lane 2
05. Ligation control: ligase +, adapter +, using fill-in control of lane 2
06. Ligation control: ligase +, adapter −, using fill-in
07. Ligation with ligase, adapter using fill-in DNA
Protection assay
08 and 09. protection assay : exo − or +, respectively, using DNA run on lane 4
10 and 11. protection assay : exo − or +, respectively, using DNA run on lane 5
12 and 13. protection assay : exo − or +, respectively, using DNA run on lane 6
14 and 15. protection assay : exo − or +, respectively, using DNA run on lane 7

FIG. 11

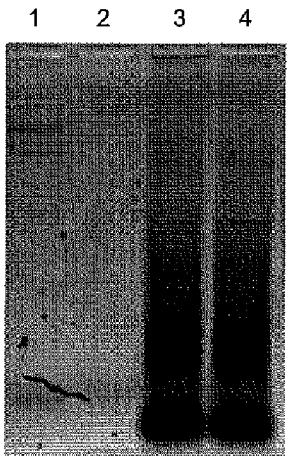

Lane 1 : T3RNAP -, DNaseI –
Lane 2 : T3RNAP -, DNaseI +
Lane 3 : T3RNAP +, DNaseI –
Lane 4 : T3RNAP +, DNaseI +

SEQ ID NO: 9

5' GGGAGAAGCCAAUCGAGGAGAAGAGAGGgaucnn... nnnnn...

...nnGAUCCCUCUCUUCUCCAUCAUCACUGCUGCUUUACUAC
UGUUCUCCCUAUAGUGAGUCGUAUUACCUCCUCUCCUU – 3'  } SEQ ID NO: 10

FIG. 12

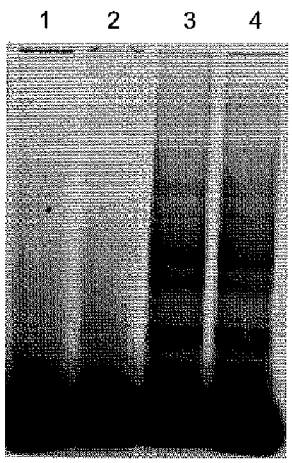

Lane 1 : RT reaction control T3RNAP -, DNaseI –
Lane 2 : RT reaction control T3RNAP -, DNaseI +
Lane 3 : RT reaction after T3RNAP +, DNaseI –
Lane 4 : RT reaction after T3RNAP +, DNaseI +

SEQ ID NO: 9

5' GGGAGAAGCCAAUCGAGGAGAAGAGAGGgaucnn...nnnnn...

...nnGAUCCCUCUCUUCUCCAUCAUCACUGCUGCUUUACUAC
UGUUCUCCCUAUAGUGAGUCGUAUUACCUCCUCUCCUU – 3'  } SEQ ID NO: 10

←──────────────
(primer)

FIG. 13

ASYMMETRIC ADAPTER LIBRARY CONSTRUCTION

CROSS REFERENCE TO RELATED APPLICATIONS

This application is a Continuation Application of U.S. Non-Provisional application Ser. No. 13/224,134 (now U.S. Pat. No. 8,288,097), filed on Sep. 1, 2011, which is a Continuation of U.S. Non-Provisional application Ser. No. 12/432,080 (U.S. Pat. No. 8,029,993), filed Apr. 29, 2009, which claims priority to U.S. Provisional Application No. 61/049,323, filed Apr. 30, 2008, all of which are herein incorporated by reference.

BACKGROUND

Numerous nucleic acid analysis processes require or are greatly facilitated by asymmetrically labeling the nucleic acids under study. For example, asymmetric tagging allows one to control subsequent manipulations and reactions with respect to one particular strand of DNA (e.g., Crick vs. Watson). One method of achieving asymmetric tagging of a nucleic acid employs DNA strand methylation by the enzyme Dam methylase (see, e.g., U.S. Pat. No. 7,217,522 and provisional U.S. Patent application 60/947,109, filed on Jun. 29, 2007, both of which are incorporated by reference herein). Alternatively, one can incorporate 5 methyl-dCTP during strand replication rather than employing Dam methylase to achieve a similar result. Another method employs various biotin labeling and pullout tricks to isolate asymmetrically labeled fragments (see, e.g., Nature vol. 437, p 376-380 (2005)).

Given the incredible expansion of nucleic acid-based assays (e.g., in the field of comparative genomics), there is a significant demand for methods that can simplify nucleic acid manipulation and analysis.

SUMMARY OF THE INVENTION

The present invention provides methods and compositions for asymmetrically tagging a nucleic acid fragment using asymmetric adapters.

Aspects of the present invention include methods of producing an asymmetrically tagged nucleic acid fragment including the steps of: i) ligating an adapter to each end of a double-stranded nucleic acid fragment, wherein the adapter includes: (a) a first and a second nucleic acid strand associated with each other via one or more complementary domains, the adapter having a first end and a second end; (b) one or more region of substantial non-complementarity between the first and second nucleic acid strands; (c) a ligation site positioned on the first end of the adapter configured to allow ligation of the adapter to the double stranded nucleic acid fragment; and (d) a hairpin structure positioned on the 3' strand on the second end of the adaptor, the hairpin structure producing a nucleic acid synthesis self-priming site; and ii) performing a first round of nucleic acid synthesis initiated from the self-priming site, thereby producing an asymmetrically tagged nucleic acid fragment.

In certain embodiments, the nucleotide polymerase used in the nucleic acid synthesis is selected from the group consisting of: a RNA polymerase, a mesophilic DNA polymerase, a reverse transcriptase, and a thermophilic DNA polymerase.

In certain embodiments, the region of substantial non-complementarity, the first and/or second nucleic acid strands include one or more of the following: a unique identifier (UID), an RNA polymerase promoter region, a primer binding site, a restriction enzyme site, and a recombination site.

In certain embodiments, the adaptor includes an RNA polymerase promoter region adjacent to the hairpin structure or within the duplex region of the hairpin structure.

In certain embodiments, the RNA promoter region is oriented such that RNA polymerization proceeds toward the hairpin structure.

In certain embodiments, the double-stranded nucleic acid fragment is produced by digesting a parent double-stranded nucleic acid sample with a restriction enzyme and polishing the ends of the resultant restriction enzyme fragments to create ends compatible with the ligation site of the adapter.

In certain embodiments, the method further includes isolating one strand of the asymmetrically tagged nucleic acid fragment.

In certain embodiments, the isolating includes treating the asymmetrically tagged nucleic acid fragment with an exonuclease selected to digest only one strand of the asymmetrically tagged nucleic acid fragment.

Aspects of the subject invention include nucleic acid adapters including: (a) a first and a second nucleic acid strand associated with each other via one or more complementary domains, the adapter having a first end and a second end; (b) one or more region of substantial non-complementarity between the first and second nucleic acid strands; (c) a ligation site positioned on the first end of the adapter configured to allow ligation of the adapter to a double stranded nucleic acid fragment; and (d) a hairpin structure positioned on the 3' strand on the second end of the adaptor, the hairpin structure producing a nucleic acid synthesis self-priming site.

In certain embodiments, the region of substantial non-complementarity in the first or second nucleic acid strand includes one or more of the following: a unique identifier (UID), an RNA polymerase promoter region, a primer binding site, a restriction enzyme site, and a recombination site.

In certain embodiments, the adaptor includes an RNA polymerase promoter region adjacent to the hairpin structure or within the duplex region of the hairpin structure.

Aspects of the present invention include methods of producing an asymmetrically tagged nucleic acid fragment, the method including: i) ligating an adapter to both ends of a double-stranded nucleic acid fragment, wherein the adapter includes: (a) a first and a second nucleic acid strand hybridized together, wherein the hybridized strands include one or more wobble base pair; (b) a ligation site positioned on a first end of the hybridized strands configured to allow ligation of the adapter to the double stranded nucleic acid fragment; and (c) a nucleic acid synthesis primer binding site positioned upstream of the one or more wobble base pair; ii) annealing a synthesis primer specific for the nucleic acid synthesis primer binding site to the adaptor ligated fragment; and iii) performing a first round of nucleic acid synthesis initiated from the annealed synthesis primer, wherein the nucleotide base incorporated at the one or more wobble base pair in the adapter region at a first end of the adaptor ligated fragment is different than the corresponding nucleotide in the adapter region at a second end of the adapter ligated fragment, thereby producing an asymmetrically tagged nucleic acid fragment.

In certain embodiments, the one or more wobble base pair is positioned within the adapter such that the resultant asymmetrically tagged nucleic acid fragment includes a restriction enzyme recognition and/or cut site at only one end.

In certain embodiments, the one or more wobble base pair is positioned within the ligation site.

In certain embodiments, the method further includes: digesting the asymmetrically tagged nucleic acid fragment with a restriction enzyme specific for the restriction enzyme recognition and/or cut site; and ligating a second, different adapter to the digested fragment, the second adapter having a ligation site compatible with the digested end of the fragment.

In certain embodiments, the method further includes isolating one strand of the asymmetrically tagged nucleic acid fragment.

In certain embodiments, the isolating includes treating the asymmetrically tagged nucleic acid fragment with an exonuclease selected to digest only one strand of the asymmetrically tagged nucleic acid fragment.

In certain embodiments, the adapter further includes one or more of the following: a unique identifier (UID), an RNA polymerase promoter region, a primer binding site, a restriction enzyme site, and a recombination site.

Aspects of the present invention include an adapter including: (a) a first and a second nucleic acid strand hybridized together, wherein the hybridized strands include one or more wobble base pair; (b) a ligation site positioned on a first end of the adapter configured to allow ligation of the adapter to a compatible end of a double stranded nucleic acid fragment; and (c) a nucleic acid synthesis primer binding site positioned upstream of the one or more wobble base pair.

In certain embodiments, the one or more wobble base pair is positioned within a restriction enzyme recognition and/or cut site in the adapter.

In certain embodiments, the adapter further includes one or more of the following: a unique identifier (UID), an RNA polymerase promoter region, a primer binding site, a restriction enzyme site, and a recombination site.

BRIEF DESCRIPTION OF THE DRAWINGS

The invention is best understood from the following detailed description when read in conjunction with the accompanying drawings. It is emphasized that, according to common practice, the various features of the drawings are not to-scale. Indeed, the dimensions of the various features are arbitrarily expanded or reduced for clarity. Included in the drawings are the following figures:

FIG. 10 shows results of experiments analyzing the structure of the asymmetric adapter shown in FIG. 8 using single stranded DNA specific exonuclease Exonuclease I and/or double stranded specific exonuclease lambda exonuclease.

FIG. 11 shows construction of a asymmetric adapter library from lambda DNA digested with BstYI.

FIG. 12 shows the pattern of in vitro transcription (IVT) reaction using the adapter library in FIG. 11 as a template.

FIG. 13 shows 1st strand cDNA synthesis from the transcripts produced in FIG. 12.

Lane 1: Primer extension from forward primer from adapter library (shown in FIG. 16A).

Lane 2: Primer extension from reverse primer from DNA as template (shown in FIG. 16B).

Lane 3: RT from reverse primer from transcribed RNA as template (shown in FIG. 16C). RNA transcribed from ds DNA extended from forward primer. Thus, the template DNA for IVT reaction has no loop structure on both ends (shown in FIG. 16A).

Lane 4: RT control for the reaction run on lane 3, No reverse transcriptase in the RT reaction.

Lane 5: RT from reverse primer from transcribed RNA as template. RNA transcribed from ds DNA annealed with forward primer. Thus, the template DNA still has loop structures on both ends containing double stranded T3 promoter region (template in FIG. 15).

Lane 6: RT control for the reaction run on lane 5, No reverse transcriptase in the RT reaction.

Figure 15:
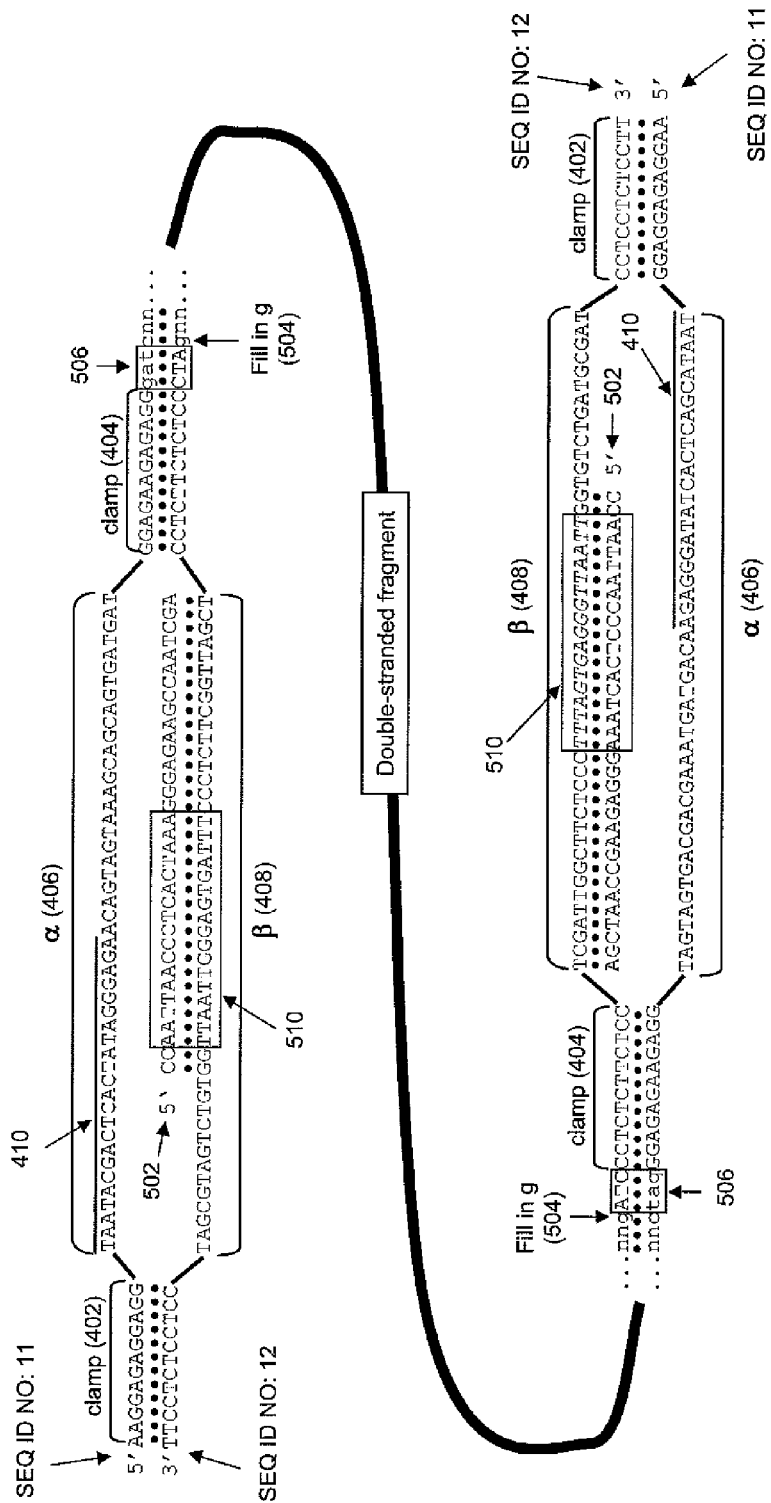

FIG. 15 shows an asymmetric adapter ligated nucleic acid fragment having an annealed primer that forms a T3 RNA polymerase promoter useful in IVT reactions.

Figure 16:
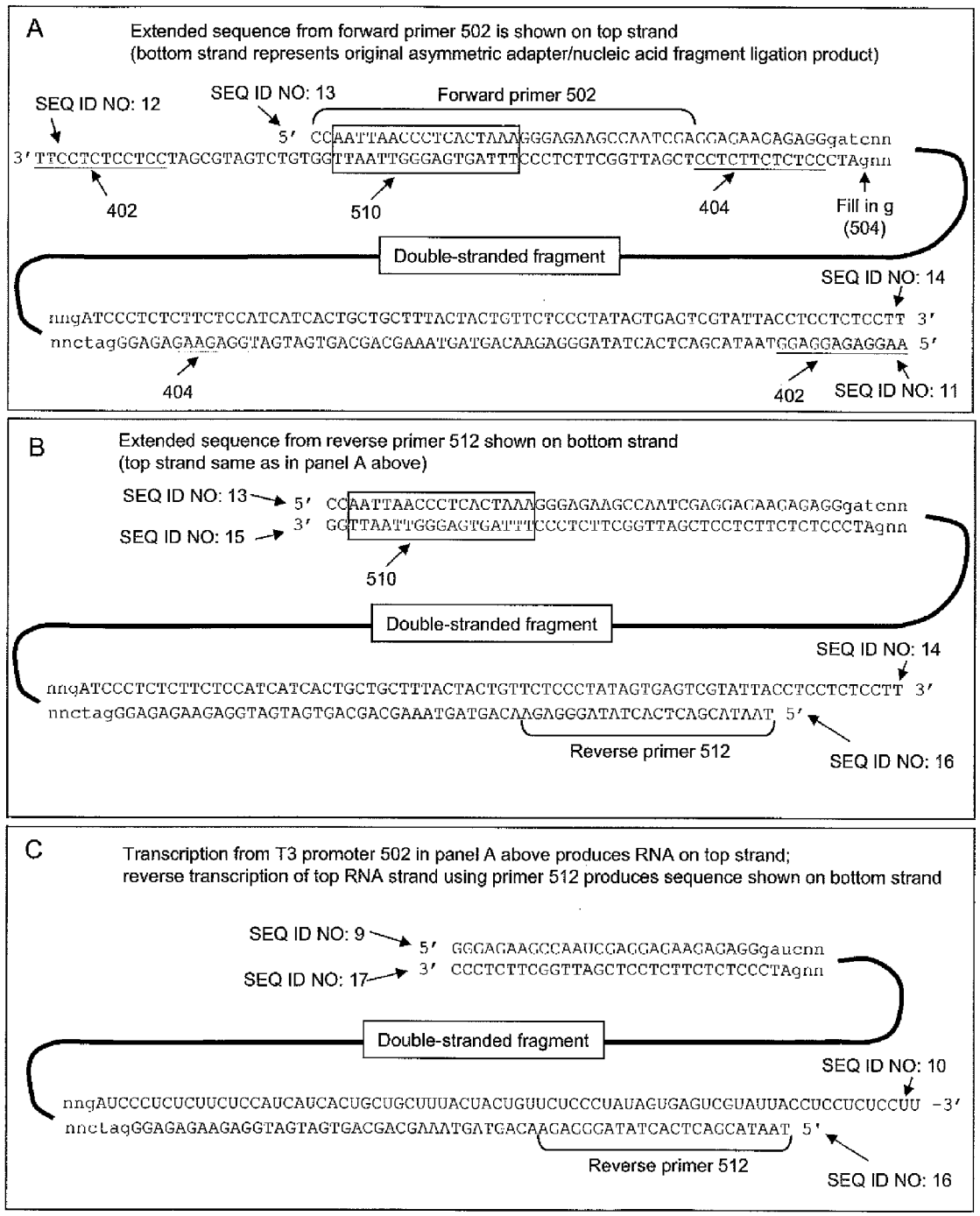

FIGS. 16A, 16B and 16C show extension products of an exemplary asymmetric adapter ligated nucleic acid fragment. 16A shows DNA polymerase extension using the bottom strand as a template and the T3 promoter primer 502. The T3 promoter site is indicated in box 510. 16B shows DNA polymerase extension using the top strand produced in 16A as a template and a reverse primer 512. 16C shows T3 RNA polymerase IVT extension using double stranded T3 promoter site 510 as shown in 16A (and in FIG. 15), followed by reverse transcriptase extension in the opposite direction using reverse primer 512.

DEFINITIONS

Unless otherwise defined, all technical and scientific terms used herein have the same meaning as commonly understood by one of ordinary skill in the art to which this invention belongs. Still, certain elements are defined for the sake of clarity and ease of reference.

Terms and symbols of nucleic acid chemistry, biochemistry, genetics, and molecular biology used herein follow those of standard treatises and texts in the field, e.g. Kornberg and Baker, DNA Replication, Second Edition (W.H. Freeman, New York, 1992); Lehninger, Biochemistry, Second Edition (Worth Publishers, New York, 1975); Strachan and Read, Human Molecular Genetics, Second Edition (Wiley-Liss, New York, 1999); Eckstein, editor, Oligonucleotides and Analogs: A Practical Approach (Oxford University Press, New York, 1991); Gait, editor, Oligonucleotide Synthesis: A Practical Approach (IRL Press, Oxford, 1984); and the like.

"Amplicon" means the product of a polynucleotide amplification reaction. That is, it is a population of polynucleotides, usually double stranded, that are replicated from one or more starting sequences. The one or more starting sequences may be one or more copies of the same sequence, or it may be a mixture of different sequences. Amplicons may be produced by a variety of amplification reactions whose products are multiple replicates of one or more target nucleic acids. Generally, amplification reactions producing amplicons are "template-driven" in that base pairing of reactants, either nucleotides or oligonucleotides, have complements in a template polynucleotide that are required for the creation of reaction products. In one aspect, template-driven reactions are primer extensions with a nucleic acid polymerase or oligonucleotide ligations with a nucleic acid ligase. Such reactions include, but are not limited to, polymerase chain reactions (PCRs), linear polymerase reactions, nucleic acid sequence-based amplification (NASBAs), rolling circle amplifications, and the like, disclosed in the following references that are incorporated herein by reference: Mullis et al, U.S. Pat. Nos. 4,683, 195; 4,965,188; 4,683,202; 4,800,159 (PCR); Gelfand et al, U.S. Pat. No. 5,210,015 (real-time PCR with "TAQMAN™" probes); Wittwer et al, U.S. Pat. No. 6,174,670; Kacian et al, U.S. Pat. No. 5,399,491 ("NASBA"); Lizardi, U.S. Pat. No. 5,854,033; Aono et al, Japanese patent publ. JP 4-262799 (rolling circle amplification); and the like. In one aspect, amplicons of the invention are produced by PCRs. An amplification reaction may be a "real-time" amplification if a detection chemistry is available that permits a reaction product to be measured as the amplification reaction progresses, e.g. "real-time PCR" described below, or "real-time NASBA" as described in Leone et al, Nucleic Acids Research, 26: 2150-2155 (1998), and like references. As used herein, the term "amplifying" means performing an amplification reaction. A "reaction mixture" means a solution containing all the necessary reactants for performing a reaction, which may include, but not be limited to, buffering agents to maintain pH at a selected level during a reaction, salts, co-factors, scavengers, and the like.

The term "assessing" includes any form of measurement, and includes determining if an element is present or not. The terms "determining", "measuring", "evaluating", "assessing" and "assaying" are used interchangeably and includes quantitative and qualitative determinations. Assessing may be relative or absolute. "Assessing the presence of" includes determining the amount of something present, and/or determining whether it is present or absent. As used herein, the terms "determining," "measuring," and "assessing," and "assaying" are used interchangeably and include both quantitative and qualitative determinations.

"Complementary" or "substantially complementary" refers to the hybridization or base pairing or the formation of a duplex between nucleotides or nucleic acids, such as, for instance, between the two strands of a double stranded DNA molecule or between an oligonucleotide primer and a primer binding site on a single stranded nucleic acid. Complementary nucleotides are, generally, A and T (or A and U), or C and G. Two single stranded RNA or DNA molecules are said to be substantially complementary when the nucleotides of one strand, optimally aligned and compared and with appropriate nucleotide insertions or deletions, pair with at least about 80% of the nucleotides of the other strand, usually at least about 90% to 95%, and more preferably from about 98 to 100%. Alternatively, substantial complementarity exists when an RNA or DNA strand will hybridize under selective hybridization conditions to its complement. Typically, selective hybridization will occur when there is at least about 65% complementary over a stretch of at least 14 to 25 nucleotides, preferably at least about 75%, more preferably at least about 90% complementary. See, M. Kanehisa Nucleic Acids Res. 12:203 (1984), incorporated herein by reference.

"Duplex" means at least two oligonucleotides and/or polynucleotides that are fully or partially complementary undergo Watson-Crick type base pairing among all or most of their nucleotides so that a stable complex is formed. The terms "annealing" and "hybridization" are used interchangeably to mean the formation of a stable duplex. "Perfectly matched" in reference to a duplex means that the poly- or oligonucleotide strands making up the duplex form a double stranded structure with one another such that every nucleotide in each strand undergoes Watson-Crick base pairing with a nucleotide in the other strand. A stable duplex can include Watson-Crick base pairing and/or non-Watson-Crick base pairing between the strands of the duplex (where base pairing means the forming hydrogen bonds). In certain embodiments, a non-Watson-Crick base pair includes a nucleoside analog, such as deoxyinosine, 2,6-diaminopurine, PNAs, LNA's and the like. In certain embodiments, a non-Watson-Crick base pair includes a "wobble base", such as deoxyinosine, 8-oxo-dA, 8-oxo-dG and the like, where by "wobble base" is meant a nucleic acid base that can base pair with a first nucleotide base in a complementary nucleic acid strand but that, when employed as a template strand for nucleic acid synthesis, leads to the incorporation of a second, different nucleotide base into the synthesizing strand (wobble bases are described in further detail below). A "mismatch" in a duplex between two oligonucleotides or polynucleotides means that a pair of nucleotides in the duplex fails to undergo Watson-Crick bonding.

"Genetic locus," "locus," or "locus of interest" in reference to a genome or target polynucleotide, means a contiguous sub-region or segment of the genome or target polynucleotide. As used herein, genetic locus, locus, or locus of interest may refer to the position of a nucleotide, a gene or a portion of a gene in a genome, including mitochondrial DNA or other non-chromosomal DNA (e.g., bacterial plasmid), or it may refer to any contiguous portion of genomic sequence whether or not it is within, or associated with, a gene. A genetic locus, locus, or locus of interest can be from a single nucleotide to a segment of a few hundred or a few thousand nucleotides in length or more. In general, a locus of interest will have a reference sequence associated with it (see description of "reference sequence" below).

"Kit" refers to any delivery system for delivering materials or reagents for carrying out a method of the invention. In the context of reaction assays, such delivery systems include systems that allow for the storage, transport, or delivery of reaction reagents (e.g., probes, enzymes, etc. in the appropriate containers) and/or supporting materials (e.g., buffers, written instructions for performing the assay etc.) from one location to another. For example, kits include one or more enclosures (e.g., boxes) containing the relevant reaction reagents and/or supporting materials. Such contents may be delivered to the intended recipient together or separately. For example, a first container may contain an enzyme for use in an assay, while a second container contains probes.

"Ligation" means to form a covalent bond or linkage between the termini of two or more nucleic acids, e.g. oligonucleotides and/or polynucleotides, in a template-driven reaction. The nature of the bond or linkage may vary widely and the ligation may be carried out enzymatically or chemically. As used herein, ligations are usually carried out enzymatically to form a phosphodiester linkage between a 5' carbon of a terminal nucleotide of one oligonucleotide with 3' carbon of another oligonucleotide. A variety of template-driven ligation reactions are described in the following references, which are incorporated by reference: Whiteley et al, U.S. Pat. No. 4,883,750; Letsinger et al, U.S. Pat. No. 5,476,930; Fung et al, U.S. Pat. No. 5,593,826; Kool, U.S. Pat. No. 5,426,180; Landegren et al, U.S. Pat. No. 5,871,921; Xu and Kool, Nucleic Acids Research, 27: 875-881 (1999); Higgins et al, Methods in Enzymology, 68: 50-71 (1979); Engler et al, The Enzymes, 15: 3-29 (1982); and Namsaraev, U.S. patent publication 2004/0110213.

"Nucleoside" as used herein includes the natural nucleosides, including T-deoxy and 2'-hydroxyl forms, e.g. as described in Kornberg and Baker, DNA Replication, 2nd Ed. (Freeman, San Francisco, 1992). "Analogs" in reference to nucleosides includes synthetic nucleosides having modified base moieties and/or modified sugar moieties, e.g. described by Scheit, Nucleotide Analogs (John Wiley, New York, 1980); Uhlman and Peyman, Chemical Reviews, 90: 543-584 (1990), or the like, with the proviso that they are capable of specific hybridization. Such analogs include synthetic nucleosides designed to enhance binding properties, reduce complexity, increase specificity, and the like. Polynucleotides comprising analogs with enhanced hybridization or nuclease resistance properties are described in Uhlman and Peyman (cited above); Crooke et al, Exp. Opin. Ther. Patents, 6: 855-870 (1996); Mesmaeker et al, Current Opinion in Structual Biology, 5: 343-355 (1995); and the like. Exemplary types of polynucleotides that are capable of enhancing duplex stability include oligonucleotide N3'→P5' phosphoramidates (referred to herein as "amidates"), peptide nucleic acids (referred to herein as "PNAs"), oligo-2'-O-alkylribonucleotides, polynucleotides containing C-5 propynylpyrimidines, locked nucleic acids ("LNAs"), and like compounds. Such oligonucleotides are either available commercially or may be synthesized using methods described in the literature.

"Polymerase chain reaction," or "PCR," means a reaction for the in vitro amplification of specific DNA sequences by the simultaneous primer extension of complementary strands of DNA. In other words, PCR is a reaction for making multiple copies or replicates of a target nucleic acid flanked by primer binding sites, such reaction comprising one or more repetitions of the following steps: (i) denaturing the target nucleic acid, (ii) annealing primers to the primer binding sites, and (iii) extending the primers by a nucleic acid polymerase in the presence of nucleoside triphosphates. Usually, the reaction is cycled through different temperatures optimized for each step in a thermal cycler instrument. Particular temperatures, durations at each step, and rates of change between steps depend on many factors well-known to those of ordinary skill in the art, e.g. exemplified by the references: McPherson et al, editors, PCR: A Practical Approach and PCR2: A Practical Approach (IRL Press, Oxford, 1991 and 1995, respectively). For example, in a conventional PCR using Taq DNA polymerase, a double stranded target nucleic acid may be denatured at a temperature >90° C., primers annealed at a temperature in the range 50-75° C., and primers extended at a temperature in the range 72-78° C. The term "PCR" encompasses derivative forms of the reaction, including but not limited to, RT-PCR, real-time PCR, nested PCR, quantitative PCR, multiplexed PCR, and the like. Reaction volumes range from a few hundred nanoliters, e.g. 200 nL, to a few hundred μL, e.g. 200 μL. "Reverse transcription PCR," or "RT-PCR," means a PCR that is preceded by a reverse transcription reaction that converts a target RNA to a complementary single stranded DNA, which is then amplified, e.g. Tecott et al, U.S. Pat. No. 5,168,038, which patent is incorporated herein by reference. "Real-time PCR" means a PCR for which the amount of reaction product, i.e. amplicon, is monitored as the reaction proceeds. There are many forms of real-time PCR that differ mainly in the detection chemistries used for monitoring the reaction product, e.g. Gelfand et al, U.S. Pat. No. 5,210,015 ("TAQMAN™"); Wittwer et al, U.S. Pat. Nos. 6,174,670 and 6,569,627 intercalating dyes); Tyagi et al, U.S. Pat. No. 5,925,517 (molecular beacons); which patents are incorporated herein by reference. Detection chemistries for real-time PCR are reviewed in Mackay et al, Nucleic Acids Research, 30: 1292-1305 (2002), which is also incorporated herein by reference. "Nested PCR" means a two-stage PCR wherein the amplicon of a first PCR becomes the sample for a second PCR using a new set of primers, at least one of which binds to an interior location of the first amplicon. As used herein, "initial primers" in reference to a nested amplification reaction mean the primers used to generate a first amplicon, and "secondary primers" mean the one or more primers used to generate a second, or nested, amplicon. "Multiplexed PCR" means a PCR wherein multiple target sequences (or a single target sequence and one or more reference sequences) are simultaneously carried out in the same reaction mixture, e.g. Bernard et al, Anal. Biochem., 273: 221-228 (1999)(two-color real-time PCR). Usually, distinct sets of primers are employed for each sequence being amplified.

"Quantitative PCR" means a PCR designed to measure the abundance of one or more specific target sequences in a sample or specimen. Quantitative PCR includes both absolute quantitation and relative quantitation of such target sequences. Quantitative measurements are made using one or more reference sequences that may be assayed separately or together with a target sequence. The reference sequence may be endogenous or exogenous to a sample or specimen, and in the latter case, may comprise one or more competitor templates. Typical endogenous reference sequences include segments of transcripts of the following genes: β-actin, GAPDH, $β_2$-microglobulin, ribosomal RNA, and the like. Techniques for quantitative PCR are well-known to those of ordinary skill in the art, as exemplified in the following references that are incorporated by reference: Freeman et al, Biotechniques, 26: 112-126 (1999); Becker-Andre et al, Nucleic Acids Research, 17: 9437-9447 (1989); Zimmerman et al, Biotechniques, 21: 268-279 (1996); Diviacco et al, Gene, 122: 3013-3020 (1992); Becker-Andre et al, Nucleic Acids Research, 17: 9437-9446 (1989); and the like.

"Polynucleotide" or "oligonucleotide" is used interchangeably and each mean a linear polymer of nucleotide monomers. Monomers making up polynucleotides and oligonucleotides are capable of specifically binding to a natural polynucleotide by way of a regular pattern of monomer-to-monomer interactions, such as Watson-Crick type of base pairing, base stacking, Hoogsteen or reverse Hoogsteen types of base pairing, wobble base pairing, or the like. As described in detail below, by "wobble base" is meant a nucleic acid base that can base pair with a first nucleotide base in a complementary nucleic acid strand but that, when employed as a template strand for nucleic acid synthesis, leads to the incorporation of a second, different nucleotide base into the synthesizing strand. Such monomers and their internucleosidic linkages may be naturally occurring or may be analogs thereof, e.g. naturally occurring or non-naturally occurring analogs. Non-naturally occurring analogs may include peptide nucleic acids (PNAs, e.g., as described in U.S. Pat. No. 5,539,082, incorporated herein by reference), locked nucleic acids (LNAs, e.g., as described in U.S. Pat. No. 6,670,461, incorporated herein by reference), phosphorothioate internucleosidic linkages, bases containing linking groups permitting the attachment of labels, such as fluorophores, or haptens, and the like. Whenever the use of an oligonucleotide or polynucleotide requires enzymatic processing, such as extension by a polymerase, ligation by a ligase, or the like, one of ordinary skill would understand that oligonucleotides or polynucleotides in those instances would not contain certain analogs of internucleosidic linkages, sugar moieties, or bases at any or some positions. Polynucleotides typically range in size from a few monomeric units, e.g. 5-40, when they are usually referred to as "oligonucleotides," to several thousand monomeric units. Whenever a polynucleotide or oligonucleotide is represented by a sequence of letters (upper or lower case), such as "ATGCCTG," it will be understood that the nucleotides are in 5'→3' order from left to right and that "A" denotes deoxyadenosine, "C" denotes deoxycytidine, "G" denotes deoxyguanosine, and "T" denotes thymidine, "I" denotes deoxyinosine, "U" denotes uridine, unless otherwise indicated or obvious from context. Unless otherwise noted the terminology and atom numbering conventions will follow those disclosed in Strachan and Read, Human Molecular Genetics 2 (Wiley-Liss, New York, 1999). Usually polynucleotides comprise the four natural nucleosides (e.g. deoxyadenosine, deoxycytidine, deoxyguanosine, deoxythymidine for DNA or their ribose counterparts for RNA) linked by phosphodiester linkages; however, they may also comprise non-natural nucleotide analogs, e.g. including modified bases, sugars, or internucleosidic linkages. It is clear to those skilled in the art that where an enzyme has specific oligonucleotide or polynucleotide substrate requirements for activity, e.g. single stranded DNA, RNA/DNA duplex, or the like, then selection of appropriate composition for the oligonucleotide or polynucleotide substrates is well within the knowledge of one of ordinary skill, especially with guidance from treatises, such as Sambrook et al, Molecular Cloning, Second Edition (Cold Spring Harbor Laboratory, New York, 1989), and like references.

"Primer" means an oligonucleotide, either natural or synthetic, that is capable, upon forming a duplex with a polynucleotide template, of acting as a point of initiation of nucleic acid synthesis and being extended from its 3' end along the template so that an extended duplex is formed. The sequence of nucleotides added during the extension process is determined by the sequence of the template polynucleotide. Usually primers are extended by a DNA polymerase. Primers are generally of a length compatible with its use in synthesis of primer extension products, and are usually are in the range of between 8 to 100 nucleotides in length, such as 10 to 75, 15 to 60, 15 to 40, 18 to 30, 20 to 40, 21 to 50, 22 to 45, 25 to 40, and so on, more typically in the range of between 18-40, 20-35, 21-30 nucleotides long, and any length between the stated ranges. Typical primers can be in the range of between 10-50 nucleotides long, such as 15-45, 18-40, 20-30, 21-25 and so on, and any length between the stated ranges. In some embodiments, the primers are usually not more than about 10, 12, 15, 20, 21, 22, 23, 24, 25, 26, 27, 28, 29, 30, 35, 40, 45, 50, 55, 60, 65, or 70 nucleotides in length.

Primers are usually single-stranded for maximum efficiency in amplification, but may alternatively be double-stranded. If double-stranded, the primer is usually first treated to separate its strands before being used to prepare extension products. This denaturation step is typically affected by heat, but may alternatively be carried out using alkali, followed by neutralization. Thus, a "primer" is complementary to a template, and complexes by hydrogen bonding or hybridization with the template to give a primer/template complex for initiation of synthesis by a polymerase, which is extended by the addition of covalently bonded bases linked at its 3' end complementary to the template in the process of DNA synthesis.

A "primer pair" as used herein refers to first and second primers having nucleic acid sequence suitable for nucleic acid-based amplification of a target nucleic acid. Such primer pairs generally include a first primer having a sequence that is the same or similar to that of a first portion of a target nucleic acid, and a second primer having a sequence that is complementary to a second portion of a target nucleic acid to provide for amplification of the target nucleic acid or a fragment thereof. Reference to "first" and "second" primers herein is arbitrary, unless specifically indicated otherwise. For example, the first primer can be designed as a "forward primer" (which initiates nucleic acid synthesis from a 5' end of the target nucleic acid) or as a "reverse primer" (which initiates nucleic acid synthesis from a 5' end of the extension product produced from synthesis initiated from the forward primer). Likewise, the second primer can be designed as a forward primer or a reverse primer.

"Readout" means a parameter, or parameters, which are measured and/or detected that can be converted to a number or value. In some contexts, readout may refer to an actual numerical representation of such collected or recorded data. For example, a readout of fluorescent intensity signals from a microarray is the address and fluorescence intensity of a signal being generated at each hybridization site of the microarray; thus, such a readout may be registered or stored in various ways, for example, as an image of the microarray, as a table of numbers, or the like.

"Solid support", "support", and "solid phase support" are used interchangeably and refer to a material or group of materials having a rigid or semi-rigid surface or surfaces. In many embodiments, at least one surface of the solid support will be substantially flat, although in some embodiments it may be desirable to physically separate synthesis regions for different compounds with, for example, wells, raised regions, pins, etched trenches, or the like. According to other embodiments, the solid support(s) will take the form of beads, resins, gels, microspheres, or other geometric configurations. Microarrays usually comprise at least one planar solid phase support, such as a glass microscope slide.

"Specific" or "specificity" in reference to the binding of one molecule to another molecule, such as a labeled target sequence for a probe, means the recognition, contact, and formation of a stable complex between the two molecules, together with substantially less recognition, contact, or complex formation of that molecule with other molecules. In one aspect, "specific" in reference to the binding of a first molecule to a second molecule means that to the extent the first molecule recognizes and forms a complex with another molecule in a reaction or sample, it forms the largest number of the complexes with the second molecule. Preferably, this largest number is at least fifty percent. Generally, molecules involved in a specific binding event have areas on their surfaces or in cavities giving rise to specific recognition between the molecules binding to each other. Examples of specific binding include antibody-antigen interactions, enzyme-substrate interactions, formation of duplexes or triplexes among polynucleotides and/or oligonucleotides, receptor-ligand interactions, and the like. As used herein, "contact" in reference to specificity or specific binding means two molecules are close enough that weak noncovalent chemical interactions, such as Van der Waal forces, hydrogen bonding, base-stacking interactions, ionic and hydrophobic interactions, and the like, dominate the interaction of the molecules.

As used herein, the term "$T_m$" is used in reference to the "melting temperature." The melting temperature is the temperature (as measured in ° C.) at which a population of double-stranded nucleic acid molecules becomes half dissociated into single strands. Several equations for calculating the Tm of nucleic acids are well known in the art. As indicated by standard references, a simple estimate of the Tm value in degrees Celsius may be calculated by the equation, Tm=81.5+0.41 (% G+C), when a nucleic acid is in aqueous solution at 1 M NaCl (see e.g., Anderson and Young, Quantitative Filter Hybridization, in Nucleic Acid Hybridization (1985). Other references (e.g., Allawi, H. T. & SantaLucia, J., Jr., Biochemistry 36, 10581-94 (1997)) include alternative methods of computation which take structural and environmental, as well as sequence characteristics into account for the calculation of Tm.

"Sample" means a quantity of material from a biological, environmental, medical, or patient source in which detection, measurement, or labeling of target nucleic acids is sought. On the one hand it is meant to include a specimen or culture (e.g., microbiological cultures). On the other hand, it is meant to include both biological and environmental samples. A sample may include a specimen of synthetic origin. Biological samples may be animal, including human, fluid, solid (e.g., stool) or tissue, as well as liquid and solid food and feed products and ingredients such as dairy items, vegetables, meat and meat by-products, and waste. Biological samples may include materials taken from a patient including, but not limited to cultures, blood, saliva, cerebral spinal fluid, pleural fluid, milk, lymph, sputum, semen, needle aspirates, and the like. Biological samples may be obtained from all of the various families of domestic animals, as well as feral or wild animals, including, but not limited to, such animals as ungulates, bear, fish, rodents, etc. Environmental samples include environmental material such as surface matter, soil, water and industrial samples, as well as samples obtained from food and dairy processing instruments, apparatus, equipment, utensils, disposable and non-disposable items. These examples are not to be construed as limiting the sample types applicable to the present invention.

The terms "upstream" and "downstream" in describing nucleic acid molecule orientation and/or polymerization are used herein as understood by one of skill in the art. As such, "downstream" generally means proceeding in the 5' to 3' direction, i.e., the direction in which a nucleotide polymerase normally extends a sequence, and "upstream" generally means the converse. For example, a first primer that hybridizes "upstream" of a second primer on the same target nucleic acid molecule is located on the 5' side of the second primer (and thus nucleic acid polymerization from the first primer proceeds towards the second primer).

It is further noted that the claims may be drafted to exclude any optional element. As such, this statement is intended to serve as antecedent basis for use of such exclusive terminology as "solely", "only" and the like in connection with the recitation of claim elements, or the use of a "negative" limitation.

DETAILED DESCRIPTION OF THE INVENTION

The invention is drawn to asymmetrically tagging one or more nucleic acids in a sample using asymmetric adapters.

Before the present invention is described, it is to be understood that this invention is not limited to particular embodiments described, as such may, of course, vary. It is also to be understood that the terminology used herein is for the purpose of describing particular embodiments only, and is not intended to be limiting, since the scope of the present invention will be limited only by the appended claims.

Where a range of values is provided, it is understood that each intervening value, to the tenth of the unit of the lower limit unless the context clearly dictates otherwise, between the upper and lower limits of that range is also specifically disclosed. Each smaller range between any stated value or intervening value in a stated range and any other stated or intervening value in that stated range is encompassed within the invention. The upper and lower limits of these smaller ranges may independently be included or excluded in the range, and each range where either, neither or both limits are included in the smaller ranges is also encompassed within the invention, subject to any specifically excluded limit in the stated range. Where the stated range includes one or both of the limits, ranges excluding either or both of those included limits are also included in the invention.

Unless defined otherwise, all technical and scientific terms used herein have the same meaning as commonly understood by one of ordinary skill in the art to which this invention belongs. Although any methods and materials similar or equivalent to those described herein can be used in the practice or testing of the present invention, some potential and preferred methods and materials are now described. All publications mentioned herein are incorporated herein by reference to disclose and describe the methods and/or materials in connection with which the publications are cited. It is understood that the present disclosure supersedes any disclosure of an incorporated publication to the extent there is a contradiction.

It must be noted that as used herein and in the appended claims, the singular forms "a", "an", and "the" include plural referents unless the context clearly dictates otherwise. Thus, for example, reference to "a nucleic acid" includes a plurality of such nucleic acids and reference to "the compound" includes reference to one or more compounds and equivalents thereof known to those skilled in the art, and so forth.

The practice of the present invention may employ, unless otherwise indicated, conventional techniques and descriptions of organic chemistry, polymer technology, molecular biology (including recombinant techniques), cell biology, biochemistry, and immunology, which are within the skill of the art. Such conventional techniques include polymer array synthesis, hybridization, ligation, and detection of hybridization using a label. Specific illustrations of suitable techniques can be had by reference to the example herein below. However, other equivalent conventional procedures can, of course, also be used. Such conventional techniques and descriptions can be found in standard laboratory manuals such as *Genome Analysis: A Laboratory Manual Series* (Vols. I-IV), *Using Antibodies: A Laboratory Manual, Cells: A Laboratory Manual, PCR Primer: A Laboratory Manual, and Molecular Cloning: A Laboratory Manual* (all from Cold Spring Harbor Laboratory Press), Stryer, L. (1995) *Biochemistry* (4th Ed.) Freeman, New York, Gait, "*Oligonucleotide Synthesis: A Practical Approach*" 1984, IRL Press, London, Nelson and Cox (2000), Lehninger, A., *Principles of Biochemistry* $3^{rd}$ Ed., W. H. Freeman Pub., New York, N.Y. and Berg et al. (2002) *Biochemistry*, $5^{th}$ Ed., W. H. Freeman Pub., New York, N.Y., all of which are herein incorporated in their entirety by reference for all purposes.

The publications discussed herein are provided solely for their disclosure prior to the filing date of the present application. Nothing herein is to be construed as an admission that the present invention is not entitled to antedate such publication by virtue of prior invention. Further, the dates of publication provided may be different from the actual publication dates which may need to be independently confirmed.

As summarized above, the present invention provides methods and compositions for asymmetrically tagging a nucleic acid fragment using asymmetric adapters.

Methods of Asymmetrically Tagging a Nucleic Acid Fragment

Starting Nucleic Acids

Nucleic acids in a nucleic acid sample being analyzed (or processed) in accordance with the present invention can be from any nucleic acid source. As such, nucleic acids in a nucleic acid sample can be from virtually any nucleic acid source, including but not limited to genomic DNA, complementary DNA (cDNA), RNA (e.g., messenger RNA, ribosomal RNA, short interfering RNA, microRNA, etc.), plasmid DNA, mitochondrial DNA, etc. Furthermore, as any organism can be used as a source of nucleic acids to be processed in accordance with the present invention, no limitation in that regard is intended. Exemplary organisms include, but are not limited to, plants, animals (e.g., reptiles, mammals, insects, worms, fish, etc.), bacteria, fungi (e.g., yeast), viruses, etc. In certain embodiments, the nucleic acids in the nucleic acid sample are derived from a mammal, where in certain embodiments the mammal is a human.

In certain embodiments, the nucleic acids in the nucleic acid sample are enriched prior to analysis. By enriched is meant that the nucleic acid is subjected to a process that reduces the complexity of the nucleic acids, generally by increasing the relative concentration of particular nucleic acid species in the sample (e.g., having a specific locus of interest, including a specific nucleic acid sequence, lacking a locus or sequence, being within a specific size range, etc.). There are a wide variety of ways to enrich nucleic acids having a specific characteristic(s) or sequence, and as such any convenient method to accomplish this may be employed.

In certain embodiments, nucleic acids in the nucleic acid sample are amplified prior to analysis. In certain of these embodiments, the amplification reaction also serves to enrich a starting nucleic acid sample for the locus of interest. For example, a starting nucleic acid sample can be subjected to a polymerase chain reaction (PCR) that amplifies one or more region of interest. In certain embodiments, the amplification reaction is an exponential amplification reaction whereas in certain other embodiments, the amplification reaction is a linear amplification reaction. Any convenient method for performing amplification reactions on a starting nucleic acid sample can be used in practicing the subject invention. In certain embodiments, the nucleic acid polymerase employed in the amplification reaction is a polymerase that has proofreading capability (e.g., phi29 DNA Polymerase, *Thermococcus litoralis* DNA polymerase, *Pyrococcus furiosus* DNA polymerase, etc.).

In certain embodiments, the nucleic acid sample being analyzed is derived from a single source (e.g., a single organism, tissue, cell, subject, etc.), whereas in other embodiments, the nucleic acid sample is a pool of nucleic acids extracted from a plurality of sources (e.g., a pool of nucleic acids from a plurality of organisms, tissues, cells, subjects, etc.), where by "plurality" is meant two or more. As such, in certain embodiments, a nucleic acid sample can contain nucleic acids from 2 or more sources, 3 or more sources, 5 or more sources, 10 or more sources, 50 or more sources, 100 or more sources, 500 or more sources, 1000 or more sources, 5000 or more sources, up to and including about 10,000 or more sources. As described above, the nucleic acids in nucleic acid samples from a single source as well as from multiple sources include a locus of interest for which at least one reference sequence is known.

In certain embodiments, nucleic acid fragments tagged according to aspects of the subject invention are to be pooled with nucleic acid fragments derived from a plurality of sources (e.g., a plurality of organisms, tissues, cells, subjects, etc.), where by "plurality" is meant two or more. In such embodiments, the asymmetric adapter employed for each separate nucleic acid sample may include a uniquely identifying tag (UID) such that after the tagging process is complete, the source from which the each tagged nucleic acid fragment was derived can be determined. Any type of UID can be used, including but not limited to those described in co-pending U.S. patent application Ser. No. 11/656,746, filed on Jan. 22, 2007, and titled "Nucleic Acid Analysis Using Sequence Tokens", as well as U.S. Pat. No. 7,393,665, issued on Jul. 1, 2008, and titled "Methods and Compositions for Tagging and Identifying Polynucleotides", both of which are incorporated herein by reference in their entirety for their description of nucleic acid tags and their use in identifying polynucleotides. In certain embodiments, a set of UIDs employed to tag a plurality of samples need not have any particular common property (e.g., $T_m$, length, base composition, etc.), as the asymmetric tagging methods (and many tag readout methods, including but not limited to sequencing of the tag or measuring the length of the tag) can accommodate a wide variety of unique UID sets.

Asymmetric Adapter

Asymmetric adapters that find use in the present invention may have a variety of structural configurations, examples of which are described below.

1. Asymmetric Adapters Having a Region of Substantial Non-Complementarity

In certain embodiments, an asymmetric adapter includes one or more clamp regions, a ligation site and a region of substantial non-complementarity such that when a asymmetric adapter is ligated to both ends of a nucleic acid fragment and the adapter-ligated fragment is amplified (or replicated) through the region of non-complementarity, the resultant nucleic acid fragments are tagged asymmetrically, i.e., the nucleic acid fragment(s) produced have a different tag sequence on each end. By different tag sequence on each end is meant that a tag sequence on one end of a nucleic acid fragment produced according to methods of the present invention has at least one region or domain that has a nucleic acid sequence that is different from a tag sequence on the other end. Embodiments of each of these features will be described in further detail below.

Figure 1:
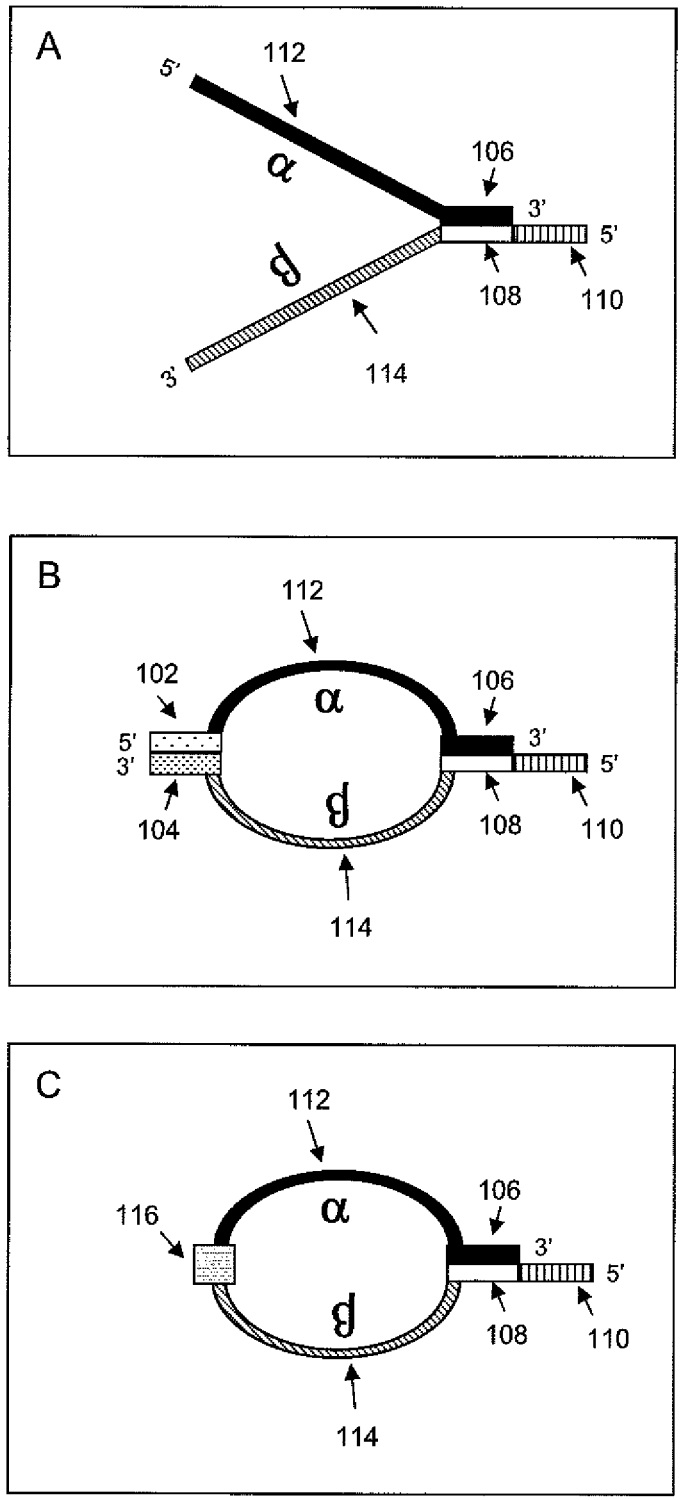
FIGS. 1A, 1B and 1C show exemplary structural components of asymmetric adapters that find use in practicing aspects of the subject invention.

FIG. 1 shows three embodiments for asymmetric adapter structures that find use in the present invention. The asymmetric adapter in FIG. 1A includes two nucleic acid strands: a top strand having elements 112 and 106 in a 5' to 3' orientation, and a bottom strand having elements 114, 108 and 110 in a 3' to 5' orientation. As is evident from the structure shown in FIG. 1A, elements 106 and 108 hybridize to one another forming a first clamp region that, when ligated to a compatible end of a nucleic acid fragment via ligation site 110 (discussed below), is proximal to the nucleic acid fragment (also referred to as "inner"). As such, the sequence of element 106 is complementary to the sequence of element 108. The asymmetric adapter in FIG. 1B also includes two nucleic acid strands: a top strand having elements 102, 112, and 106 in a 5' to 3' orientation, and a bottom strand having elements 104, 114, 108, and 110 in a 3' to 5' orientation. As with the structure shown in FIG. 1A, elements 106 and 108 in FIG. 1B hybridize to one another forming a first clamp region that is proximal to the nucleic acid fragment once ligated thereto (also referred to as "inner"). Unlike the asymmetric adapter in FIG. 1A, the asymmetric adapter in FIG. 1B includes elements 102 and 104 which hybridize to one another forming a second clamp region that is distal to the nucleic acid fragment (also referred to as "outer"). As such, the sequence of element 102 is complementary to the sequence of element 104 and the sequence of element 106 is complementary to the sequence of element 108. The length of such complementary regions which form clamp structures in the asymmetric adapters can vary and, in certain embodiments, can be affected by other sequences in the asymmetric adapter, e.g., the region of substantial non-complementarity. In certain embodiments the length of the complementary sequence is from 6 nucleotides to 50 nucleotides. For example, predictions based on a 2-state hybridization model indicate that 6 bases of complementarity (having the sequence 5' CTCCTC 3' on the top strand) would be sufficient to form a proximal camp region under the following conditions: 50 mM NaCl, 10 mM $MgCl_2$, 10 uM adapter at 20° C.

The asymmetric adapter shown in FIG. 1C is similar to the one in FIG. 1B except that rather than the second clamp region being formed from a hybridization region between the top and bottom strands, a cleavable linker 116 is used to join the 5' end of the top strand with the 3' end of the bottom strand. In embodiments that employ an asymmetric adapter with a cleavable linker as the distal clamp region, the cleavable linker is cleaved prior to any subsequent extension steps performed on the asymmetric adapter tagged fragments (see description of exemplary method below). Any convenient cleavable linker can be employed, including nucleic acid, peptide or other chemical linkers that are uniquely sensitive to a cleaving agent. By uniquely sensitive is meant that only the cleavable linker (or specific region or chemical bond in the cleavable linker) is cleaved when a asymmetric adapter ligated nucleic acid fragment is contacted to the cleaving agent. For example, a cleavable linker that includes ribonucleic acids can be cleaved by contacting an asymmetric adapter ligated DNA fragment to RNase I. As another example, a cleavable linker that includes a disulfide bond can be cleaved by contacting a asymmetric adapter ligated DNA fragment to a reducing agent such as dithiothreitol.

The asymmetric adapter structures in FIGS. 1A, 1B and 1C include one or more region of substantial non-complementarity represented by elements 112 and 114 (denoted as regions α and β, respectively). This region is also referred to herein as the "asymmetric" region. By substantially non-complementary is meant that one or both of elements 112 and 114 include at least one region of nucleic acid sequence that is not complementary to the other strand, where in certain embodiments the asymmetric adapter includes 2, 3, 4, 5, or 6 or more regions of non-complementarity. The length and identity of the one or more region of non-complementarity will vary based on the desires of the user (e.g., based on the downstream analyses to be performed on the resultant asymmetrically tagged nucleic acid). For example, in certain embodiments, elements 112 and 114 (or α and β) include one or more particular sequences which are useful for later steps in the workflow. Such sequences include, but are not limited to, restriction enzyme sites, PCR primer binding sites, linear amplification primer sites, reverse transcription primer sites, RNA polymerase promoter sites (such as for T7, T3 or SP6 RNA polymerase), UID tags (e.g., tags employed to mark the nucleic acid fragment as being derived from a specific starting sample), sequencing primer sites, etc.

It is noted here that the UID tag need only be a DNA sequence which uniquely identifies the sample or sample region from which the fragment so labeled originates. It is noted here that there are no constraints with regard to members of a set of tags being employed in the present invention. For example, a set of identity tags that finds use in the subject invention need not have similar thermodynamic or physical properties between them, e.g., be isothermal.

As indicated above, the asymmetric adapters include a ligation site 110 that is adjacent to the first, proximal clamp region (formed by 106 and 108). The ligation site comprises a region of single-strandedness that selectively associates with a compatible end of the nucleic acid fragments. The compatible region of single-strandedness may be on the bottom strand, forming a 5' overhang (as shown in FIG. 1) or, in certain embodiments, be present on the top strand, forming a 3' overhang. In order to promote ligation of the asymmetric adapter to a compatible nucleic acid fragment, the 5' end of the ligation site is phosphorylated (not shown in FIG. 1). Therefore, as described above and shown in FIG. 1, the ligation site is configured to allow ligation of a asymmetric adapter to a compatible end of a nucleic acid fragment which is to be asymmetrically tagged.

In certain embodiments, compatible ends of a nucleic acid fragment are produced by contacting a parent nucleic acid sample with a restriction enzyme and polishing the ends (e.g., by adding a single base). As such, in these embodiments, the restriction enzyme generates nucleic acid fragments having cut sites on the ends that are compatible to the single stranded region of the asymmetric adapter, i.e., the ends of the nucleic acid fragments have regions of complementarity to the region of single-strandedness (i.e., the overhang regions at the cut site) in the ligation site of the asymmetric adapter. In this way, the asymmetric adapter ligation site and compatible ends of the nucleic acid fragments can be ligated to one another under appropriate ligation conditions (e.g., in the presence of an enzyme having DNA ligase activity in appropriate buffering conditions and co-factors). See, e.g., FIG. 3, described in detail below.

In certain embodiments, compatible ends of the nucleic acid fragments are not produced by restriction enzyme digestion. For example, a parental nucleic acid sample can be fragmented by applying shear forces to the sample, which leads to fragmented DNA. Polishing of the ends of such fragmented DNA can then be performed to produce blunt ends having no 5' or 3' overhang (e.g., by filling in and or removing overhangs as is known in the art). Asymmetric adapters compatible with such blunt-end fragments will themselves be blunt ended at the ligation site and have a 5' phosphate group. In these embodiments, the blunt ends of the fragmented nucleic acid are de-phosphorylated to prevent inter-fragment ligation.

In certain other embodiments, a blunt end nucleic acid fragment(s), whether produced by shearing or by a restriction enzyme the produced blunt ends, is contacted with a DNA polymerase that can add a single specific nucleotide in a non-template dependent manner (e.g., an added dA to the 3' end of blunt fragment using Taq polymerase). The compatible asymmetric adapter in such embodiments will be designed to have a compatible end containing a single base overhang that is complementary to the nucleotide added to the blunt ends of the fragment (e.g., the asymmetric adapter ligation site will have a 3' dT overhang). This embodiment is akin to TA cloning systems employed for cloning Taq polymerase produced PCR products.

As is clear from the description above, any convenient method for creating compatible ends between nucleic acid fragments and asymmetric adapters to promote ligation of the asymmetric adapter while reducing inter-fragment ligation may be used.

Figure 2:
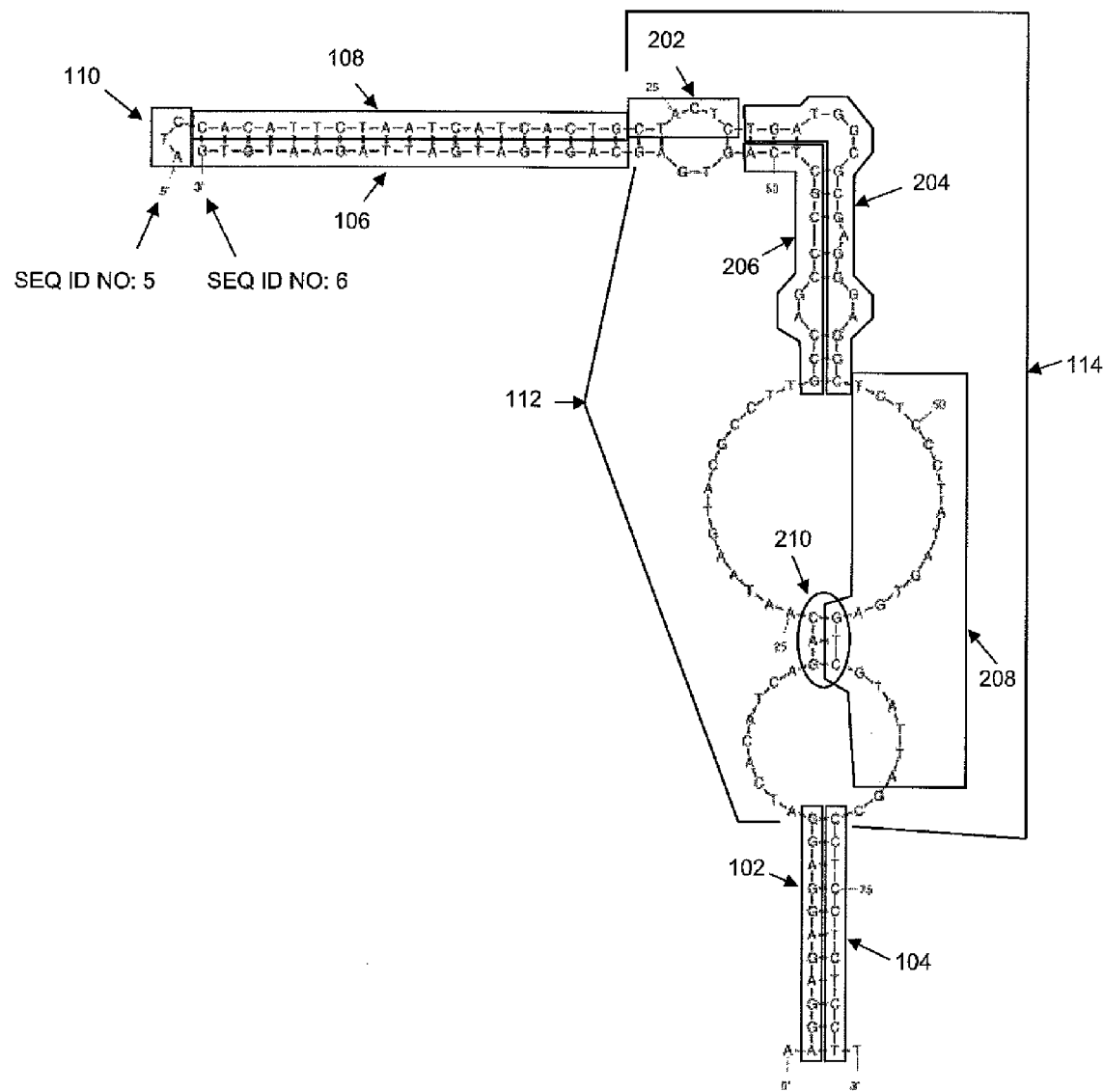
FIG. 2 shows the sequence, secondary structure and domains of a specific example of an asymmetric adapter that finds use in practicing aspects of the subject invention.

FIG. 2 shows the secondary and domain structure of an exemplary asymmetric adapter that finds use in aspects of the present invention. The asymmetric adapter in FIG. 2 includes two strands of DNA that associate to form two clamp regions, the first of which is formed by complementary sequences 108 and 106 and the second of which is formed by complementary sequences 102 and 104 (with the element numbers corresponding to those in FIG. 1). The asymmetric also includes a ligation site 110 and a region of substantial non-complementarity (112 and 114). Within this region of substantial non-complementarity (or asymmetric region), the asymmetric adapter includes a number of specific elements that are useful for downstream analyses. These include: an identify tag region 202; sequencing primer sites A and B (204 and 206, respectively; e.g., for use in Roche 454 sequencing method); and a T7 promoter region 208. As indicated above, virtually any functional domain or sequence of interest can be included in the region of substantial non-complementarity, which, in general, will be determined by a user based on the downstream assay(s) to be performed on the resultant asymmetrically tagged nucleic acid fragment.

As can be seen in FIG. 2, the region of substantial non-complementarity may have small sub-domains in which duplex DNA forms. For example, in T7 promoter region 208, there is a stretch of three bases 210 that form a duplex between the strands. As such, while in certain exemplary diagrams the region of substantial non-complementarity (the asymmetric region) is shown as having no nucleic acid duplex structures, in certain embodiments, some nucleic acid duplex structures will form.

Figure 3:
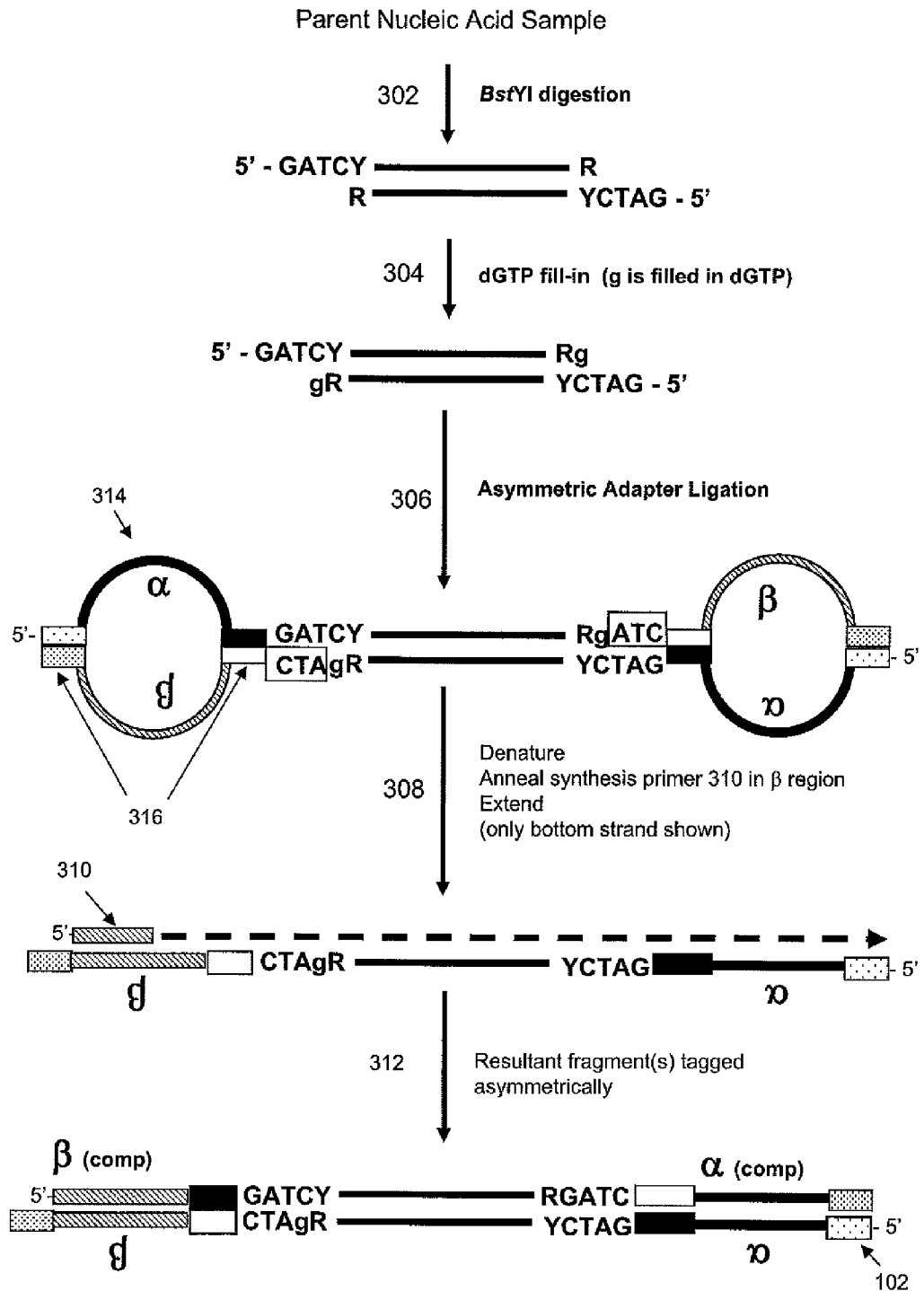
FIG. 3 shows an exemplary embodiment of producing asymmetrically tagged nucleic acid fragments according to aspects of the subject invention.

FIG. 3 shows steps in an exemplary method for asymmetrically tagging a nucleic acid fragment according to aspects of the subject invention.

In this exemplary method, a parent nucleic acid sample containing starting nucleic acid (e.g., genomic DNA) is digested in step 302 with a restriction enzyme (in this case BstYI) producing 5' overhang GATC (BstYI has a recognition site of R/GATCY, where R is a purine and Y is a pyrimidine as conventionally denoted in the art and the slash indicating the position of the cut site). At step 304, the 5' GATC overhang is filled in with dG on the bottom strand (shown as "g"), producing a 5' GAT overhang. This overhang represents the compatible end of the nucleic acid fragment that will serve as a ligation site for a suitably designed asymmetric adapter (i.e., one having a 5' ATC overhang). The fill-in step 304 prevents the restriction-digested, double-stranded fragments of the starting nucleic acid sample from being ligated to each other during the asymmetric adapter ligation step (i.e., prevents inter-fragment ligation).

It is noted here that there are numerous ways in which to produce nucleic acid fragments having ends compatible with an asymmetric adapter. Producing compatible ends may include, but is not limited to, cutting with a restriction enzyme, shearing the nucleic acid, adding one or more nucleotides, removing one or more nucleotides, and adding or removing a phosphate group. The process of generating compatible ends on a nucleic acid fragment is sometimes referred to herein as "polishing". The resultant compatible ends can have blunt or sticky ends (i.e., having compatible overhang regions), both terms being well known in the art.

In certain embodiments, a nucleic acid fragment may be ligated to two independent and distinct asymmetric adapters, each of which is ligated to a different compatible end of a nucleic acid fragment. Any convenient method for producing a nucleic acid fragment(s) having more than one distinct compatible end can be employed. In certain of these embodiments, the different compatible ends of the nucleic acid fragment are produced by digesting the nucleic acid fragment with more than one restriction enzyme. These multiply-digested fragments are ligated to separate asymmetric adapters, each of which will ligate to one of the compatible ends. The ligation of these asymmetric adapters can be sequential or simultaneous. In addition, more than two asymmetric adapters may be used to tag a nucleic acid sample containing multiple fragments with any variety of different compatible ends. This will depend on the desires of the user and the specific analyses to be performed on the resultant asymmetrically tagged nucleic acid fragments.

In step 306, asymmetric adapter 314 having 5'ATC overhang (shown in the box) is ligated to the nucleic acid fragments having compatible 5'GAT overhangs on both ends. The asymmetric adapters shown include two clamp regions 316 (proximal and distal, with respect to their position relative to the nucleic acid fragment once ligated to it) formed by compatible ends of the two strands of the asymmetric adapter. The top strand of the asymmetric adapter includes a region of substantial non-complementarity designated as $\alpha$ and the bottom strand of the asymmetric includes a region of substantial non-complementarity designated as $\beta$. In other words, $\alpha$ and $\beta$ are not fully complementary sequences, and as such do not form a continuous hybridized structure. As described above, regions $\alpha$ and $\beta$ may include specific regions that facilitate or allow specific downstream analyses as desired by a user of the method.

In step 308, the adapter ligated nucleic acid fragment(s) is moderately denatured in the asymmetric region and a synthesis primer 310 is annealed in the $\beta$ region. Only the bottom strand of the asymmetric adapter ligated nucleic acid fragment is shown here. In certain embodiments, the $\beta$ region in the top strand will also have an annealed primer 310 in the $\beta$ region.

Once annealed, the synthesis primer is extended by contacting the asymmetric adapter tagged nucleic acid fragment with a nucleotide polymerase under nucleic acid polymerizing conditions to produce an asymmetrically tagged nucleic acid fragment in step 312. Specifically, the resultant nucleic acid fragment includes a $\beta$ region and its complement [$\beta$ (comp) in FIG. 3] (or a substantial portion of the region, depending on where the synthesis primer 310 binding site is located) on one end and an $\alpha$ region and its complement [$\alpha$ (comp) in FIG. 3] on the other. In certain embodiments, the extension reaction is a linear amplification reaction while in other embodiments the extension is an exponential amplification reaction (e.g., a conventional PCR reaction). Any convenient method for extending/amplifying the asymmetric adapter tagged nucleic acid fragment that will produce an asymmetrically tagged nucleic acid can be employed, including DNA polymerization or RNA polymerization.

Once extended, the now asymmetrically tagged nucleic acid fragment can be manipulated and assayed as desired by the user. As noted above, functional regions or domains in the substantially non-complementary regions of the asymmetric adapter can facilitate such downstream analyses (e.g., sequencing, amplification, sorting based on an identity tag, etc.).

In certain embodiments, the method may include isolating only one strand of an asymmetric adapter ligated nucleic acid fragment, and as such, only one strand will be processed in downstream steps. For example, one can treat the asymmetrically tagged DNA shown on the bottom of FIG. 3 with Exonuclease III to remove the top strand of the duplex. As is well know in the art, Exonuclease III catalyzes the stepwise removal of mononucleotides from 3'-hydroxyl termini of double-stranded DNA. Due to the location of priming of synthesis primer 310 (i.e., in the β region, which is several bases in from the 3' end of the template strand), the asymmetrically tagged duplex DNA at the bottom of FIG. 3 has a 3' single stranded overhang on the left side but not on the right side. Because Exonuclease III will only digest double stranded DNA in the 3' to 5' direction, only the top strand is sensitive to this enzyme, with digestion proceeding from the right side (i.e., from the "a complement" side).

As another example, T7 exonuclease can be employed to remove the bottom strand of the asymmetrically tagged DNA shown at the bottom of FIG. 3. As is known in the art, T7 exonuclease catalyzes the removal of 5' mononucleotides from double-stranded DNA in the 5' to 3' direction. If synthesis primer 310 is designed to incorporate a T7 exonuclease blocking moiety (e.g., three or more phosphorothioate linkages), the activity of T7 exonuclease can be blocked from the left side of the adapter-ligated fragment. The right side of the adapter-ligated fragment, however, does not include the T7 exonuclease blocking moiety in element 102 of the adapter, and thus is sensitive to the 5' to 3' exonuclease activity of T7 exonuclease. Thus, only the bottom strand is sensitive to this enzyme, with digestion proceeding from the right side (i.e., from the "α" side). Conversely, the top strand can be removed with T7 exonuclease if element 102 of the adapter includes a T7 exonuclease blocking moiety (element 102 is the same as shown in FIG. 1B).

In other embodiments, Lambda Exonuclease can be used to remove one strand of an adapter ligated fragment. As is known in the art, Lambda Exonuclease catalyzes the removal of 5' mononucleotides from 5'-phosphorylated double-stranded DNA. Thus, including a 5' phosphate on the 5' end of the outer region of the adapter (i.e., on the 5' end of 102), only the bottom strand of the adapter ligated fragment shown on the bottom of FIG. 3 will be degraded, leaving the top strand intact. To remove the top strand of this adapter ligated fragment with lambda exonuclease, synthesis primer 310 can include a 5' phosphate. The phosphorylation of either the asymmetric adapter or the synthesis primer 310 can be done synthetically or enzymatically (e.g., with T4 polynucleotide kinase).

In certain other embodiments, primer 310 includes a member of a binding pair, e.g., a biotin moiety at its 5' end, which can be used to immobilize the top strand on a streptavidin moiety bound to a solid support. Removal of the hybridized, non-biotinylated strand (the bottom strand) by denaturation using heat or high pH serves to isolate the biotinylated top strand.

The implementation of a single strand isolation step using the methods described above or variations thereof (or any other convenient single strand isolation step) will generally be based on the desires of the user.

Figure 4:
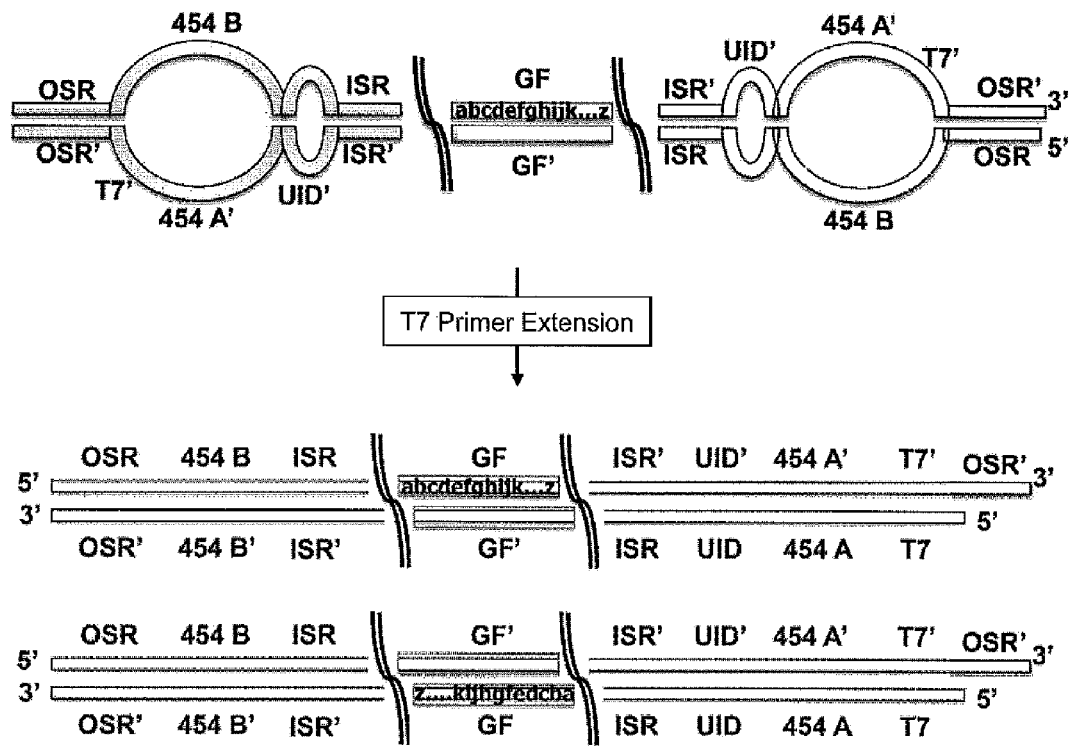
FIG. 4 shows an exemplary embodiment of an asymmetrically tagged genomic fragment (GF) in which the adapter contains specific elements.

FIG. 4 shows an exemplary tagged nucleic acid fragment in which the asymmetric adapter contains certain specific functional regions. FIG. 4 shows a genomic fragment (GF strand and complementary GF' strand) ligated to an asymmetric adapter at both ends, where the asymmetric adapter contains a number of specific functional elements and regions. As shown, the adapter contains an outer clamp region (OCR) and an inner clamp region (ICR) with an asymmetric region therebetween. One strand of this asymmetric region includes a sequencing primer binding site for next generation sequencing (454B element; used in the Roche 454 sequencing system), while the other strand of this asymmetric region includes a sequence complementary to a second sequencing primer binding site (454A'; also used in the Roche 454 sequencing system), a sequence complementary to a T7 promoter site (T7'), and a sequence complementary to a UID tag (UID'; the "prime" symbol in this figure indicates a region that is complementary to the noted functional region of interest).

Replication of this asymmetrically-tagged genome fragment with a T7 primer results in the two different double stranded fragments: the first of which represents replication of the top strand of the adapter ligated fragment and the second of which represents replication of the bottom strand of the adapter ligated fragment (the bottom strand replication product is shown in reverse orientation). As can be seen in FIG. 4, the replication of asymmetrically tagged genome fragments produces products having both orientations of the genomic fragment with respect to the tags on the end. This is illustrated in FIG. 4B by the a to z orientation of the GF/GF' regions.

Figure 5:
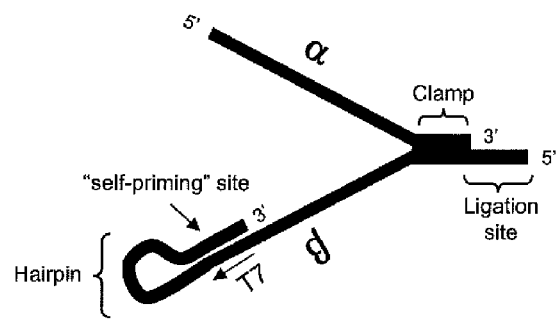
FIG. 5 shows another exemplary embodiment of an asymmetric adapter according to aspects of the present invention. This adapter is similar to the "Y" adapter as shown in FIG. 1A but includes a hairpin structure on the 3' end of the asymmetric region.

FIG. 5 shows another exemplary embodiment of an asymmetric adapter according to aspects of the present invention. This adapter is similar to the "Y" adapter as shown in FIG. 1A but includes a hairpin structure on the 3' end of the asymmetric region (i.e., opposite end from the ligation site). This hairpin structure allows for self-priming of the first round of replication from the 3' end (e.g., by a DNA polymerase), forming double-stranded products having a hairpin at one end (not shown). This hairpin structure can be exploited for further downstream process steps, including in amplification of the resultant tagged fragments. As discussed in detail above, asymmetric adapters can include any number of additional functional elements. As but one example, the inclusion of a T7 promoter site oriented such that RNA polymerization proceeds in the direction of the hairpin ("T7", as shown in FIG. 5, where the arrow indicates the direction of RNA polymerization) allows for specific isothermal amplification processes to be carried, e.g., as described in detail in U.S. patent application Ser. No. 11/338,533 filed on Jan. 23, 2006 entitled "Isothermal DNA Amplification", incorporated by reference herein in its entirety. It is noted that the T7 promoter site may be present in the hairpin structure of the adapter as shown in FIG. 5 or in the single-stranded portion of the β region (as replication from the self-priming site will reconstitute a fully functional T7 promoter). Although not shown in FIG. 5, asymmetric adapters having a hairpin structure at the 3' end opposite the ligation site may include more than one clamp region (e.g., an asymmetric adapter as shown in FIG. 1B with the addition of a 3' hairpin on the end opposite the ligation site).

2. Asymmetric Adapters Having Wobble Bases

In certain embodiments, an asymmetric adapter includes a ligation site (as described in detail above) and one or more wobble base. By "wobble base" is meant a nucleic acid base that can base pair with a first nucleotide base in a complementary nucleic acid strand but that, when employed as a template strand for nucleic acid synthesis, leads to the incorporation of a second, different nucleotide base into the synthesizing strand. Non-limiting examples of such wobble bases include: 8-oxo-dA, which can base pair with dG in a complementary strand but will lead to the incorporation of dT at the corresponding position when used as a template for nucleic acid synthesis; 8-oxo-dG, which can base pair with dA in a complementary strand but will lead to the incorporation of dG at the corresponding position when used as a template for nucleic acid synthesis; and deoxy-inosine (dI), which can base pair with any of dG, dA, dC or dT (or dN) in a complementary strand but will lead to the incorporation of dC at the corresponding position when used as a template for nucleic acid synthesis. Any convenient wobble base may be used in the adapters of the present invention.

Figure 6:
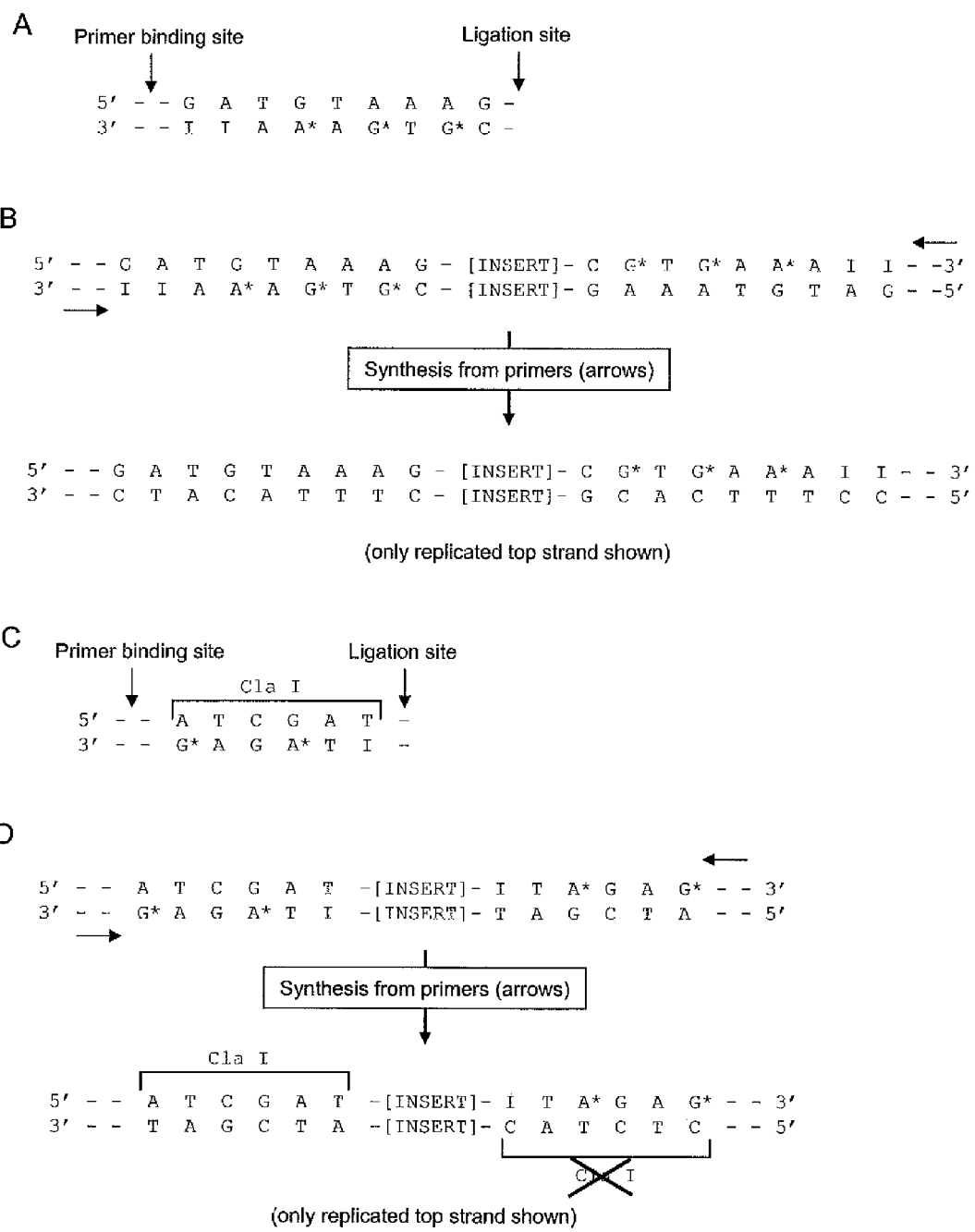
FIG. 6 shows exemplary embodiments of asymmetric adapters with wobble bases. A and B show how wobble bases produce asymmetrically tagged fragments after replication. C and D show how wobble bases can be employed to generate fragments having asymmetrically positioned restriction enzyme sites.

The presence of one or more wobble base in an asymmetric adapter allows the production of asymmetrically tagged nucleic acids after a first round of nucleic acid synthesis. This basic concept is shown in FIG. 6, where the asymmetric adapter is shown in 6A. In this exemplary asymmetric adapter, I represents inosine, A* represents 8-oxo-dA and G* represent 8-oxo-dG. While this exemplary adapter has all of the wobble bases in the bottom strand, any configuration of wobble bases may be used, including one or more wobble bases in the top strand, in the bottom strand (as shown) or in both the top and bottom strand. The number, type and position of wobble bases in an asymmetric adapter will depend on the desires of the user and generally will be based on downstream steps and analyses to be performed. Also indicated in this adapter are a nucleic acid synthesis primer binding site and a ligation site, both of which have been described in detail above.

FIG. 6B shows the asymmetric adapter in 6A attached to both ends of a nucleic acid fragment (denoted as "insert" in this figure) and the resultant replicated product produced by nucleic acid synthesis from a primer that binds to the primer binding site of the asymmetric adapter (primers shown as arrows). The resultant nucleic acid synthesis product shown is only for replication of the top strand of the asymmetric adapter-ligated fragment. As can be seen in FIG. 6B, the left end adapter of the replicated top strand now includes the sequence: 5'-G A T G T A A A G-3' while the corresponding sequence in the right end adapter has the sequence: 5'-C C T T T C A C G-3'. This fragment is thus asymmetrically labeled.

In certain embodiments, the primer employed for nucleic acid synthesis is modified such that it can be used to purify the replicated strand (the strand having asymmetric adapters) from the original template strand (e.g., the primer may include a binding moiety, e.g., a biotin, which can be purified using a corresponding binding partner, e.g., streptavidin, as discussed above). In certain other embodiments, the synthesis primer is immobilized on a solid substrate, thereby producing a solid support bound replication product.

The wobble base (or bases) may be present one or more specific elements of the asymmetric adapter, including, but not limited to, promoter regions, primer binding sites, restriction enzyme recognition/cut sites, ligation sites, UID tags, etc.

In certain embodiments, at least one wobble base (or bases) is present in a restriction enzyme recognition/cut site in the asymmetric adapter such that upon replication, a functional restriction enzyme cut site will be present on only one side of the asymmetrically labeled fragment. An exemplary embodiment is shown in FIG. 6C, where this embodiment is generally employed for inserts that do not include a Cla I site (e.g., where the restriction enzyme Cla I is used to fragment the genomic DNA). In this embodiment, the restriction site Cla I is present in the top strand of the adapter with wobble bases I (inosine), 8-oxo-dA (A*) and 8-oxo-dG (G*) present in the bottom strand. Positions of the synthesis primer binding site and the ligation site are also indicated. After ligation to a fragment and one round of replication using a corresponding synthesis primer (arrow) (FIG. 6D), the Cla I site is preserved in the adapter on the left side of the replicated fragment shown (the replicated top strand) but is lost in the adapter on the right side of the fragment. The presence of an asymmetric restriction enzyme site allows for a variety of unique manipulations of the tagged fragment. For example, the restriction site can be employed as a site to place a second adapter onto the fragment, where this second adapter includes sequences not present in the first adapter. Specifically, asymmetrically tagged fragments having a restriction site present on only one end can be cleaved with the restriction enzyme (e.g., Cla I as show in FIG. 6D) followed by ligation of a complementary, second adapter at this site. As discussed above in the example employing BstYI restriction sites, a single nucleotide fill-in reaction may also be similarly employed prior to the ligation of the second adapter to prevent undesirable ligation reactions between compatible fragment ends (with Cla I, which leaves 5'CG overhang, one could fill in with C and ligate adapters having 5'G overhang).

In certain embodiments, rather than destruction of a restriction enzyme site present in an adapter as described above, a new restriction enzyme site can be created using wobble bases. For example, an adapter having a top strand containing the sequence 5'-A G G G A T-3' paired with a bottom strand having a corresponding sequence 5'-A T C I A* T-3' (where I is inosine and A* is 8-oxo dA) would reconstitute a ClaI site asymmetrically after replication (not shown in the figures).

Figure 7:
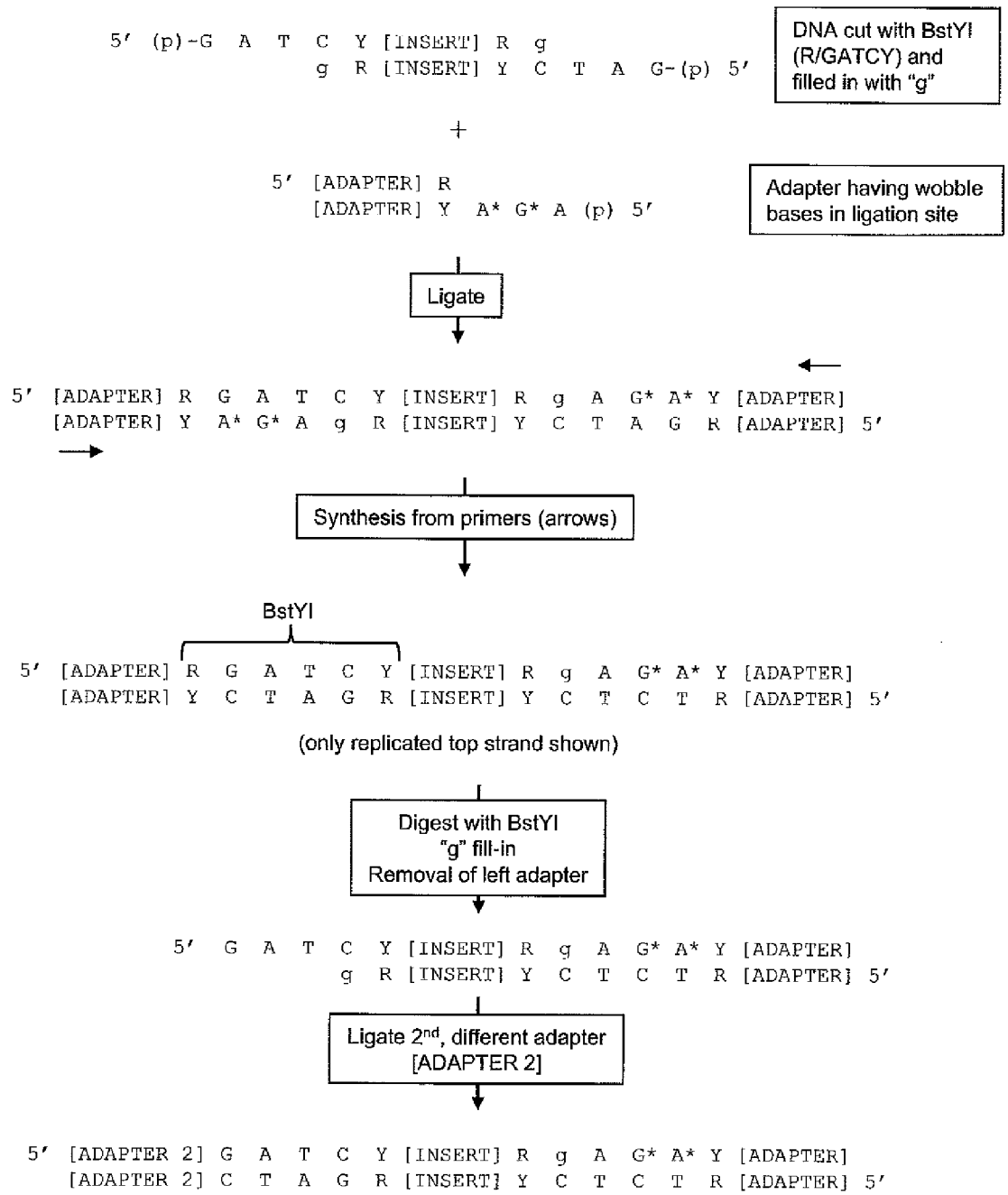
FIG. 7 shows an exemplary embodiment of an adapter having wobble bases positioned within the ligation site of the adapter followed by ligation of a second, different adapter.

In certain embodiments, the wobble base is present in the ligation site of the adapter. An exemplary embodiment is shown in FIG. 7. In this figure, DNA fragments are produced by digestion with BstYI followed by a fill-in reaction with dGTP (added base shown in small letter "g" in FIG. 7), which prevents fragment co-ligation in the subsequent ligation reaction (as described above). A generic fragment is shown at the top of FIG. 7. An adapter that includes two wobble bases (denoted A* and G*, which are 8-oxo dA and 8-oxo dG, respectively) are then ligated to both ends of these fragments. A first round of replication these adapter-fragment complexes using primers that prime in the adapter region (shown as arrows) produces products in which the BstYI restriction site is regenerated on only one end of the fragments (left side as shown in the exemplary fragment in FIG. 7; note the absence of a BstYI site at the right end of the fragment). This asymmetric restriction site can be used as a site for ligating a second, different adapter if desired by digestion with BstYI, removal of the left end adapter (e.g., using a binding moiety scheme as described above, e.g., where the synthesis primer is biotinlyated facilitating removal of the left-side adapter after BstYI digestion), and ligation of a second, different adapter having at least one region with a sequence different than the first adapter (and, e.g., where the ligation is performed after a "g" fill in of the fragment as in the previous steps).

Kits and Systems

Also provided by the subject invention are kits and systems for practicing the subject methods, as described above, such as one or more asymmetric adapters, components to create compatible ends for the asymmetric adapters, and regents for generating the asymmetrically tagged fragments after asymmetric ligation (e.g., restriction enzymes, nucleotides, polymerases, primers, etc.). The various components of the kits may be present in separate containers or certain compatible components may be precombined into a single container, as desired.

The subject systems and kits may also include one or more other reagents for preparing or processing a nucleic acid sample according to the subject methods. The reagents may include one or more matrices, solvents, sample preparation reagents, buffers, desalting reagents, enzymatic reagents, denaturing reagents, where calibration standards such as positive and negative controls may be provided as well. As such, the kits may include one or more containers such as vials or bottles, with each container containing a separate component for carrying out a sample processing or preparing step and/or for carrying out one or more steps of a nucleic acid variant isolation assay according to the present invention.

In addition to above-mentioned components, the subject kits typically further include instructions for using the components of the kit to practice the subject methods, e.g., to asymmetrically tag a nucleic acid fragment(s) according to aspects of the subject methods. The instructions for practicing the subject methods are generally recorded on a suitable recording medium. For example, the instructions may be printed on a substrate, such as paper or plastic, etc. As such, the instructions may be present in the kits as a package insert, in the labeling of the container of the kit or components thereof (i.e., associated with the packaging or sub-packaging) etc. In other embodiments, the instructions are present as an electronic storage data file present on a suitable computer readable storage medium, e.g. CD-ROM, diskette, etc. In yet other embodiments, the actual instructions are not present in the kit, but means for obtaining the instructions from a remote source, e.g. via the internet, are provided. An example of this embodiment is a kit that includes a web address where the instructions can be viewed and/or from which the instructions can be downloaded. As with the instructions, this means for obtaining the instructions is recorded on a suitable substrate.

In addition to the subject database, programming and instructions, the kits may also include one or more control samples and reagents, e.g., two or more control samples for use in testing the kit.

Utility

The asymmetric nucleic acid labeling method described herein enables one to accomplish the asymmetric labeling of a nucleic acid fragment(s) of interest in only a few steps with high yield. This is a significant advantage over asymmetric labeling method known in the art. Because the subject invention finds use in any process or analysis for which asymmetric fragment labeling is desired (e.g., assays in which one needs to control subsequent manipulations and reactions with respect to one particular strand of DNA) it will be applicable to a variety of nucleic acid analyses currently being performed (e.g., high throughput sequencing assays) as well as provide a catalyst for the development of novel assays that rely on the efficient asymmetric labeling of nucleic acids. Therefore, no limitation with regard to the types of assays to which the subject invention may be applied is intended.

EXAMPLES

Example I

Asymmetric Adapter

Figure 8:
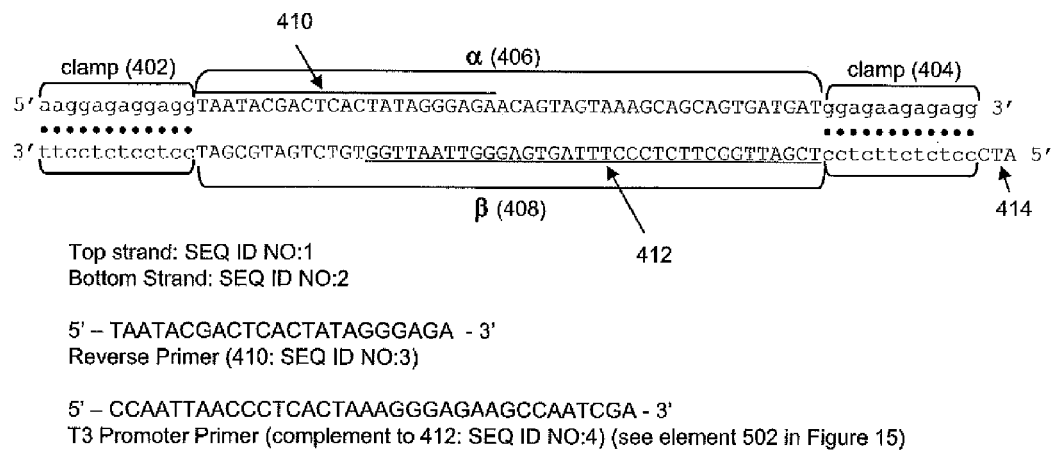
FIG. 8 shows the asymmetric adapter sequence (SEQ ID NO: 1 and SEQ ID NO: 2) and its domain structure as employed in Example 1. This specific asymmetric adapter is designed to be ligated to nucleic acid fragments having a 5' GATC overhang filled-in with dGTP. Also shown are sequences for the reverse primer (SEQ ID NO: 3) and T3 promoter primer (SEQ ID NO: 4), the use of which are described in detail in the Examples section below.

The asymmetric adapter employed is shown in FIG. 8. The top and bottom strand sequences of the asymmetric adapter are shown and include the following structural features: clamp regions 402 and 404; regions of substantial non-complementarity a (406) and β (408); and ligation site 414. The bottom strand also includes a sequence 412 that is complementary to the T3 RNA promoter while the top strand includes reverse primer sequence 410. These two elements will be used in later steps to confirm that the asymmetric adapter produces a library of asymmetrically tagged nucleic acids (i.e., the T3 promoter is on one end and the reverse primer is on the other end of the resultant asymmetrically tagged nucleic acid fragments).

The asymmetric adapter in FIG. 8 is designed to be ligated to nucleic acid fragments having a 5' GAT overhang (e.g., fragments cut with a restriction enzyme leaving a 5'GATC overhang followed by a fill-in reaction with dGTP, as shown in FIG. 3 and described above). The forward primer sequence which anneals to the underlined sequence to make T3 promoter double stranded DNA is also shown in FIG. 8 (SEQ ID NO: 4; complement to underlined sequence 412). This forward primer, when annealed to its target location in the asymmetric adapter, can be used either as a DNA synthesis primer to make double stranded DNA (e.g., as shown in FIG. 16A; e.g., for use in in vitro transcription (IVT) reactions) or as a double stranded T3 promoter site that can be used directly to produce an RNA copy of the top strand (e.g., as shown in FIG. 16C). The reverse primer, which can be used to make 1st stranded cDNA from an RNA copy of the adapter ligated fragment, is indicated in FIG. 8 (SEQ ID NO: 3; identical to underlined sequence 410).

Figure 9:
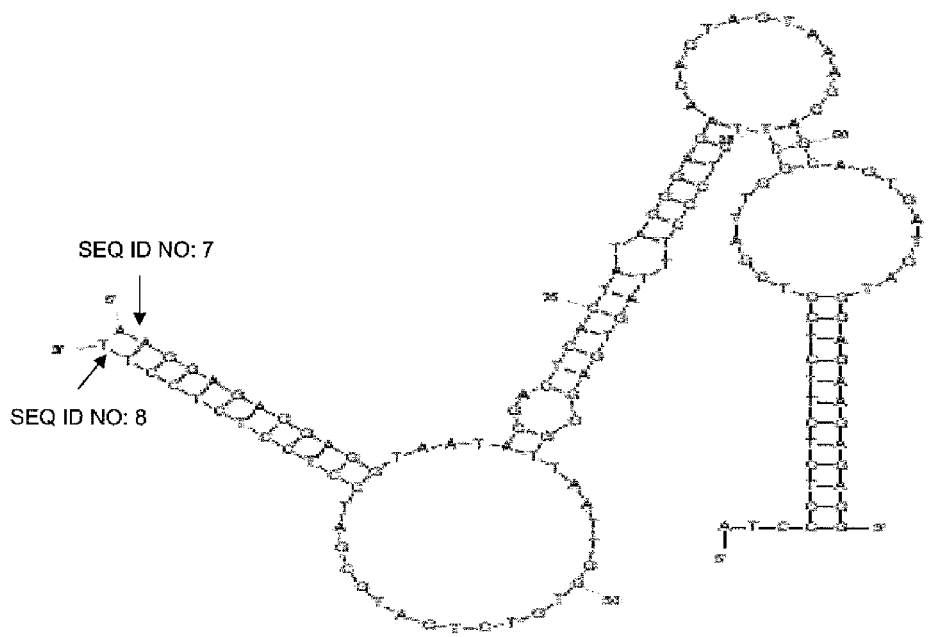
FIG. 9 shows secondary structure of the asymmetric adapter shown in FIG. 8.

FIG. 9 shows a predicted secondary structure of the asymmetric adapter in FIG. 8. Secondary structure of the asymmetric adapter was predicted by two-state hybridization model [http(colon)//dinamelt(dot)bioinfo(dot)rpi(dot)edu/twostate(dot)php] under the following conditions: 50 mM NaCl, 10 mM $MgCl_2$, 57° C., 10 uM adapter concentration. The dG and dH (often referred to as 'delta G' and 'delta H' or ΔG and ΔH) values shown at the bottom of FIG. 9 are computed from this model.

Exonuclease sensitivity of the asymmetric adapter was checked in order to confirm that the end structure of the adapter is double stranded. In addition, as the asymmetric adapter contains a large internal loop, accessibility of the ligation site 414 needed to be determined. FIG. 10 shows results of single stranded DNA specific exonuclease Exonuclease I and/or double stranded specific exonuclease lambda exonuclease treatment of the asymmetric adapter. The top strand is denoted in FIG. 10 as R and the bottom strand as T. The asymmetric adapter is thus formed by annealing strand R to strand T. As shown in this Figure, Exonuclease I did not affect the adapter migration (lane 6) but lambda exonuclease does (lane7). When both enzymes present, the asymmetric adapter is degraded (lane 8). These Exonuclease sensitivity experiments confirm that both ends of the asymmetric adapter are double stranded as predicted.

Library Production

The asymmetric adapter described above was used to make a library of asymmetrically tagged nucleic acid fragments. FIG. 11 shows a gel analysis demonstrating successful asymmetric adapter library construction from lambda DNA digested with BstYI. Lanes 1 through 7 demonstrate the importance of the single base fill-in reaction to prevent concatenation of the lambda fragments. Successful adapter ligation on both ends of each fragment is confirmed (lane 15) by the degradation sensitivity of Exonuclease I and lambda exonuclease. The 5' end of the distal side of the adapter (i.e., distal clamp region 402 as shown in FIG. 8) is lacking a phosphate group, which protects asymmetric adapter ligated DNA from lambda exonuclease degradation. Significant degradation is observed after exonuclease treatment unless the adapter is ligated (lane 13).

In Vitro Transcription (IVT)

An in vitro transcription (IVT) reaction was performed directly from the adapter library obtained in FIG. 11. The library was denatured in mild conditions to avoid complete denaturation but enough denaturation to allow access of an antisense oligonucleotide that produces a double stranded T3 promoter region (see the template shown in FIG. 15, described below). Lane 1 of FIG. 12 shows the template DNA (the same lambda library as studied in results shown in FIG. 11) for IVT; Lane 3 shows the IVT pattern from the DNA template shown in Lane 1. Lanes 2 and 4 show the template DNA treated with DNaseI or IVT reaction followed by DNaseI treatment, respectively. The proximal (5' end) and distal (3' end) sequence of transcribed RNA is shown at the bottom of FIG. 12. These results show that the T3 promoter region is successfully constructed as double stranded form (by annealing the appropriate oligonucleotide probe) and the template is utilized for transcription by T3 RNA polymerase as predicted.

First Strand cDNA Synthesis.

In order to confirm the identity of the RNA transcript produced above, reverse primer priming ability was checked by the synthesis of a first stranded cDNA. As shown in FIG. 13, the transcript strand produced above should contain the complementary sequence of reverse primer located near the 3' end of the IVT transcript produced in the previous step. FIG. 13 shows that cDNA was synthesized from the labeled reverse primer (Lanes 3 and 4). The position of the reverse primer is underlined in the sequence shown in FIG. 13 (primer designated by the arrow). This result demonstrates that the predicted strand was utilized for the IVT reaction as the transcript contains complementary sequence of the reverse primer at/near its 3' end. FIG. 16C provides a diagram of the product of the reverse transcription shown in FIG. 13. It is important to note that the RT product shown in lane 4 of FIG. 13 was produced from the DNaseI-treated IVT product shown in lane 4 of FIG. 12. Because the sample was treated with DNaseI before the RT reaction was performed, the template for the RT product shown in lane 4 of FIG. 13 can only be the IVT RNA produced in the IVT reaction from the asymmetrically tagged template.

Figure 14:
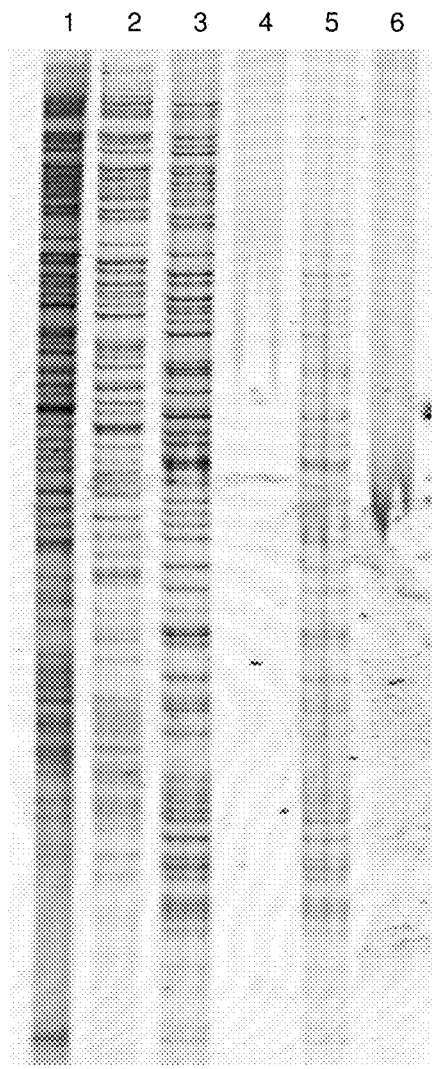
FIG. 14 shows sequencing gel analysis of synthesized first strand cDNA produced from RNA derived from IVT of asymmetrically tagged nucleic acid fragments.

The size of specific synthesis products from the BstYI lambda library using forward and reverse primers (as described above) were analyzed on a sequencing gel (a high resolution, denaturing polyacrylamide gel) to check the size distribution of each fragment (FIG. 14). Lane 1 of FIG. 14 shows the product produced by annealing a labeled forward primer (primer 502 in FIG. 15) to the lambda DNA adapter library followed by extension with Bst DNA polymerase (the expected product is the top strand shown in FIG. 16A). Lane 2 of FIG. 14 shows the product produced by annealing and extending (with Bst DNA polymerase) a labeled reverse primer to an unlabeled product produced as described for Lane 1 (the expected product is the bottom strand shown in FIG. 16B). Lane 3 of FIG. 14 shows the product of first stranded cDNA synthesis using a labeled reverse primer in an RT reaction, where the template strand is transcribed RNA produced from the T3 promoter from fully double stranded DNA (the template for T3 RNA polymerase is shown in FIG. 16A; the RNA template for the RT reaction is shown in the top strand of FIG. 16C; and the expected product is shown in the bottom strand of FIG. 16C). The expected size difference (in terms of numbers of base pairs) of each corresponding fragment between the products in Lanes 1 and 2 of FIG. 14 (also called $\Delta\frac{1}{2}$) is 12 bases ($\Delta\frac{1}{2}=12$), as the reverse primer primes at a site that is 12 nucleotides in from the end of the adapter (see binding site for the reverse primer 512 in FIG. 16B). The size difference of each corresponding fragment between lanes 2 and 3 of FIG. 14 (called $\Delta\frac{2}{3}$) is 19 bases ($\Delta\frac{2}{3}=19$), as the transcriptional start site is 19 bases from the 5' end of the forward primer, thus resulting in a template for the reverse primer that is 19 bases shorter than the template produced using the forward primer as a DNA synthesis primer (as was done for lane 2). The library fragment distribution observed in FIG. 14, lanes 1 to 3, shows the expected migration pattern: each fragment in lane 2 is shifted 12 bases down from each corresponding fragment in lane 1 and each fragment in lane 3 is sifted 19 bases down from each corresponding fragment in lane 2. These results indicate that initiation of transcription occurs from one side of the adapter ligated fragments (i.e., from the T3 promoter) while RT initiation is initiated on the other side of the adapter ligated fragments (i.e., from the reverse primer binding site). Thus, the library produced is asymmetric with respect to the adapters on the opposite ends of each fragment in the library.

Lane 5 of FIG. 14 shows the first stranded cDNA from RNA transcribed from an annealed forward primer in the adapter (as shown in FIG. 15). First stranded cDNA distribution in lane 5 is identical to that of lane 3, in which the RNA transcription template was fully double stranded DNA (as in FIG. 16C). However, the yield of 1st stranded cDNA is lower when the RNA is produced from the template shown in FIG. 15 (where the template still has regions of non-complementarity on both ends) than from the template shown in FIG. 16C (where the template has undergone at least one round of nucleic acid synthesis and thus does not include these non-complementary regions). This can be seen by comparing lanes 3 and 5.

FIG. 15 shows a possible DNA template for IVT reactions. Small letters belong to insert DNA and capitals belong to adapter sequence.

The following elements are indicated: filled in dGTP 504; 3 bases nucleotide 5' overhang ATC from adapter (ATC in box 506); distal clamp region 402 and proximal clamp region 404; annealed forward primer 502 (the T3 promoter sequence is indicated by box 510); asymmetric regions α (406) and β (408); and reverse primer sequence 410. The single, bold line connecting the adapter structures represents the double stranded nucleic acid fragment tagged with the asymmetric adapters (labeled "Double-stranded fragment").

FIG. 16A shows an adapter ligated DNA (represented as in FIG. 15, and labeled "Double-stranded fragment") that has been annealed with primer 502 of FIG. 15 (SEQ ID NO: 4) and extended by DNA polymerase. The following elements are indicated: filled in dGTP 504; 3 bases nucleotide 5' overhang ATC from adapter (ATC in box 506); distal clamp region 402 and proximal clamp region 404 (underlined in bottom strand); forward primer region 502 with T3 promoter sequence in box 510. The line connecting the adapter structures represents the nucleic acid fragment tagged with the asymmetric adapters. Original template DNA for primer extension is in the bottom strand. Small letters belong to the insert DNA, capitals belong to adapter sequence.

FIGS. 16B and 16C show extended sequences produced by reverse primer polymerization using either DNA as template and a DNA polymerase (FIG. 16B) or RNA as a template and a reverse transcriptase (FIG. 16C). The reverse primer 512 is the same as element 410 shown in FIGS. 8 and 15 (SEQ ID NO: 3).

Extended sequences from the reverse primer 512 in FIGS. 16B and 16C are shown on the bottom strand.

Although the foregoing invention has been described in some detail by way of illustration and example for purposes of clarity of understanding, it is readily apparent to those of ordinary skill in the art in light of the teachings of this invention that certain changes and modifications may be made thereto without departing from the spirit or scope of the appended claims.

Accordingly, the preceding merely illustrates the principles of the invention. It will be appreciated that those skilled in the art will be able to devise various arrangements which, although not explicitly described or shown herein, embody the principles of the invention and are included within its spirit and scope. Furthermore, all examples and conditional language recited herein are principally intended to aid the reader in understanding the principles of the invention and the concepts contributed by the inventors to furthering the art, and are to be construed as being without limitation to such specifically recited examples and conditions. Moreover, all statements herein reciting principles, aspects, and embodiments of the invention as well as specific examples thereof, are intended to encompass both structural and functional equivalents thereof. Additionally, it is intended that such equivalents include both currently known equivalents and equivalents developed in the future, i.e., any elements developed that perform the same function, regardless of structure. The scope of the present invention, therefore, is not intended to be limited to the exemplary embodiments shown and described herein, Rather, the scope and spirit of present invention is embodied by the appended claims.

The invention claimed is:

1. A method of producing asymmetrically tagged nucleic acid, comprising
   (i) ligating an adaptor to both ends of a double-stranded nucleic acid fragment to produce a ligation product, wherein said adaptor is composed of a single strand of nucleic acid that comprises:
      (a) a double stranded stem region and
      (b) a loop region that comprises a cleavable linkage that is positioned between two non-complementary sequences; and
   (ii) cleaving said ligation product using an agent that specifically cleaves said cleavable linkage, thereby producing an pair of asymmetrically tagged strands that each comprise a 5' tag and a 3' tag, where the sequences of the 5' tag and the 3' tag are different.

2. The method of claim 1, wherein said cleavable linkage is adjacent to at least one ribonucleotide.

3. The method of claim 2, wherein said cleaving is done using an RNAse.

4. The method of claim 1, wherein said RNAse is RNase 1.

5. The method of claim 1, wherein said cleavable linkage is a disulfide bond, and said cleaving is done using a reducing agent.

6. The method of claim 1, further comprising:
   iii) copying an asymmetrically tagged strand of (ii) by:
      (a) hybridizing a primer to the 3' tag sequence of the asymmetrically tagged strand of (ii); and
      (b) extending said primer using a polymerase.

7. The method of claim 6, wherein said polymerase is selected from the group consisting of: a RNA polymerase, a mesophilic DNA polymerase, a reverse transcriptase, and a thermophilic DNA polymerase.

8. The method of claim 1, wherein in said 5' tag and/or 3' tag comprises one or more of the following: a unique identifier (UID), an RNA polymerase promoter region, a primer binding site, a restriction enzyme site, and a recombination site.

9. The method of claim 1, wherein said double-stranded nucleic acid fragment is produced by shearing a parent double-stranded nucleic acid sample and polishing the ends of the resultant fragments to create ends compatible with the ends of said adapter.

10. The method of claim 1, wherein said double-stranded nucleic acid fragment is produced by digesting a parent double-stranded nucleic acid sample with a restriction enzyme and polishing the ends of the resultant restriction enzyme fragments to create ends compatible with the ends of said adapter.

11. The method of claim 1, wherein said method further comprises isolating one strand of said pair of asymmetrically tagged strands.

12. The method of claim 11, wherein said isolating comprises treating said asymmetrically tagged nucleic acid strands with an exonuclease selected to digest only one strand of said asymmetrically tagged nucleic acid strands.

13. The method of claim 1, wherein said method further comprises:
   digesting said pair of asymmetrically tagged nucleic acid strands with a restriction enzyme; and
   ligating a second, different adapter to said digested fragment, said second adapter having a ligation site compatible with the digested end of said fragment.

* * * * *

```
SEQUENCE LISTING

<160> NUMBER OF SEQ ID NOS: 17

<210> SEQ ID NO 1
<211> LENGTH: 72
<212> TYPE: DNA
<213> ORGANISM: Artificial Sequence
<220> FEATURE:
<223> OTHER INFORMATION: Asymmetric adapter sequence

<400> SEQUENCE: 1
aaggagagga ggtaatacga ctcactatag ggagaacagt agtaaagcag cagtgatgat      60
ggagaagaga gg                                                         72

<210> SEQ ID NO 2
<211> LENGTH: 75
<212> TYPE: DNA
<213> ORGANISM: Artificial Sequence
<220> FEATURE:
<223> OTHER INFORMATION: Asymmetric adapter sequence

<400> SEQUENCE: 2
atccctctct tctcctcgat tggcttctcc ctttagtgag ggttaattgg tgtctgatgc      60
gatcctcctc tcctt                                                      75

<210> SEQ ID NO 3
<211> LENGTH: 23
<212> TYPE: DNA
<213> ORGANISM: Artificial Sequence
<220> FEATURE:
<223> OTHER INFORMATION: Reverse Primer

<400> SEQUENCE: 3
taatacgact cactataggg aga                                             23

<210> SEQ ID NO 4
<211> LENGTH: 35
<212> TYPE: DNA
<213> ORGANISM: Artificial Sequence
<220> FEATURE:
<223> OTHER INFORMATION: T3 Promoter Primer

<400> SEQUENCE: 4
ccaattaacc ctcactaaag ggagaagcca atcga                                35

<210> SEQ ID NO 5
<211> LENGTH: 83
<212> TYPE: DNA
<213> ORGANISM: Artificial Sequence
<220> FEATURE:
<223> OTHER INFORMATION: Asymmetric Adapter

<400> SEQUENCE: 5
atccacattc taatcatcac tgctactctg atggcgcgag ggaggctctc cctatagtga     60
```

```
gtcgtattag ccctcctctc ctt                                            83
```

<210> SEQ ID NO 6
<211> LENGTH: 74
<212> TYPE: DNA
<213> ORGANISM: Artificial Sequence
<220> FEATURE:
<223> OTHER INFORMATION: Asymmetric Adapter

<400> SEQUENCE: 6

```
aggagaggag gatcacatca gacaataagt acgccttgcc agcccgctca gtgagcagtg    60
atgattagaa tgtg                                                      74
```

<210> SEQ ID NO 7
<211> LENGTH: 72
<212> TYPE: DNA
<213> ORGANISM: Artificial Sequence
<220> FEATURE:
<223> OTHER INFORMATION: Asymmetric Adapter

<400> SEQUENCE: 7

```
aaggagagga ggtaatacga ctcactatag ggagaacagt agtaaagcag cagtgatgat    60
ggagaagaga gg                                                        72
```

<210> SEQ ID NO 8
<211> LENGTH: 75
<212> TYPE: DNA
<213> ORGANISM: Artificial Sequence
<220> FEATURE:
<223> OTHER INFORMATION: Asymmetric Adapter

<400> SEQUENCE: 8

```
atccctctct tctcctcgat tggcttctcc ctttagtgag ggttaattgg tgtctgatgc    60
gatcctcctc tcctt                                                     75
```

<210> SEQ ID NO 9
<211> LENGTH: 34
<212> TYPE: RNA
<213> ORGANISM: Artificial Sequence
<220> FEATURE:
<223> OTHER INFORMATION: Asymmetric Adapter
<221> NAME/KEY: misc_feature
<222> LOCATION: 33, 34
<223> OTHER INFORMATION: n = A, U, C or G

<400> SEQUENCE: 9

```
gggagaagcc aaucgaggag aagagaggga ucnn                                34
```

<210> SEQ ID NO 10
<211> LENGTH: 78
<212> TYPE: RNA
<213> ORGANISM: Artificial Sequence
<220> FEATURE:
<223> OTHER INFORMATION: Asymmetric Adapter
<221> NAME/KEY: misc_feature
<222> LOCATION: 1, 2
<223> OTHER INFORMATION: n = A, U, C or G

<400> SEQUENCE: 10

```
nngauccuc ucuucuccau caucacugcu gcuuuacuac uguucucccu auagugaguc     60
guauuaccuc cucuccuu                                                  78
```

<210> SEQ ID NO 11
<211> LENGTH: 78
<212> TYPE: DNA

```
<213> ORGANISM: Artificial Sequence
<220> FEATURE:
<223> OTHER INFORMATION: Asymmetric Adapter
<221> NAME/KEY: misc_feature
<222> LOCATION: 77, 78
<223> OTHER INFORMATION: n = A,T,C or G

<400> SEQUENCE: 11
aaggagagga ggtaatacga ctcactatag ggagaacagt agtaaagcag cagtgatgat    60
ggagaagaga gggatcnn                                                  78

<210> SEQ ID NO 12
<211> LENGTH: 78
<212> TYPE: DNA
<213> ORGANISM: Artificial Sequence
<220> FEATURE:
<223> OTHER INFORMATION: Asymmetric Adapter
<221> NAME/KEY: misc_feature
<222> LOCATION: 1, 2
<223> OTHER INFORMATION: n = A,T,C or G

<400> SEQUENCE: 12
nngatccctc tcttctcctc gattggcttc tcccttagt gagggttaat tggtgtctga    60
tgcgatcctc ctctcctt                                                  78

<210> SEQ ID NO 13
<211> LENGTH: 53
<212> TYPE: DNA
<213> ORGANISM: Artificial Sequence
<220> FEATURE:
<223> OTHER INFORMATION: Asymmetric Adapter
<221> NAME/KEY: misc_feature
<222> LOCATION: 52, 53
<223> OTHER INFORMATION: n = A,T,C or G

<400> SEQUENCE: 13
ccaattaacc ctcactaaag ggagaagcca atcgaggaga agagagggat cnn           53

<210> SEQ ID NO 14
<211> LENGTH: 78
<212> TYPE: DNA
<213> ORGANISM: Artificial Sequence
<220> FEATURE:
<223> OTHER INFORMATION: Asymmetric Adapter
<221> NAME/KEY: misc_feature
<222> LOCATION: 1, 2
<223> OTHER INFORMATION: n = A,T,C or G

<400> SEQUENCE: 14
nngatccctc tcttctccat catcactgct gctttactac tgttctccct atagtgagtc    60
gtattacctc ctctcctt                                                  78

<210> SEQ ID NO 15
<211> LENGTH: 53
<212> TYPE: DNA
<213> ORGANISM: Artificial Sequence
<220> FEATURE:
<223> OTHER INFORMATION: Asymmetric Adapter
<221> NAME/KEY: misc_feature
<222> LOCATION: 1, 2
<223> OTHER INFORMATION: n = A,T,C or G

<400> SEQUENCE: 15
nngatccctc tcttctcctc gattggcttc tcccttagt gagggttaat tgg            53

<210> SEQ ID NO 16
<211> LENGTH: 66
```

-continued

```
<212> TYPE: DNA
<213> ORGANISM: Artificial Sequence
<220> FEATURE:
<223> OTHER INFORMATION: Asymmetric Adapter
<221> NAME/KEY: misc_feature
<222> LOCATION: 65, 66
<223> OTHER INFORMATION: n = A,T,C or G

<400> SEQUENCE: 16
taatacgact cactataggg agaacagtag taaagcagca gtgatgatgg agaagagagg      60 gatcnn                                                                66

<210> SEQ ID NO 17
<211> LENGTH: 34
<212> TYPE: DNA
<213> ORGANISM: Artificial Sequence
<220> FEATURE:
<223> OTHER INFORMATION: Asymmetric Adapter
<221> NAME/KEY: misc_feature
<222> LOCATION: 1, 2
<223> OTHER INFORMATION: n = A,T,C or G

<400> SEQUENCE: 17
nngatccctc tcttctcctc gattggcttc tccc                                 34
```